(12) United States Patent
Paulina et al.

(10) Patent No.: US 11,544,591 B2
(45) Date of Patent: Jan. 3, 2023

(54) FRAMEWORK FOR A COMPUTING SYSTEM THAT ALTERS USER BEHAVIOR

(71) Applicant: Google LLC, Mountain View, CA (US)

(72) Inventors: Luca Paulina, Bromley (GB); Thomas Jenkins, London (GB); Oliver Thomas Gaymond, London (GB); Nicole Kobilansky, San Francisco, CA (US); Mårten Andreas Jönsson, Malmö (SE); Mikkel Crone Koser, Copenhagen (DK)

(73) Assignee: Google LLC, Mountain View, CA (US)

( * ) Notice: Subject to any disclaimer, the term of this patent is extended or adjusted under 35 U.S.C. 154(b) by 718 days.

(21) Appl. No.: 16/547,167

(22) Filed: Aug. 21, 2019

(65) Prior Publication Data

US 2020/0065682 A1 Feb. 27, 2020

Related U.S. Application Data

(60) Provisional application No. 62/720,692, filed on Aug. 21, 2018.

(51) Int. Cl.
*G06N 5/04* (2006.01)
*G09B 19/00* (2006.01)
*G06N 20/00* (2019.01)

(52) U.S. Cl.
CPC .............. *G06N 5/04* (2013.01); *G06N 20/00* (2019.01); *G09B 19/00* (2013.01)

(58) Field of Classification Search
CPC ........... G06N 5/04; G06N 20/00; G09B 19/00
See application file for complete search history.

(56) References Cited

U.S. PATENT DOCUMENTS

| 5,864,815 A | 1/1999 | Rozak et al. |
| 6,233,560 B1 | 5/2001 | Tannenbaum |

(Continued)

FOREIGN PATENT DOCUMENTS

| EP | 3028136 A1 | 6/2016 |
| WO | 2010141802 A1 | 12/2010 |

(Continued)

OTHER PUBLICATIONS

"Voice commands for Windows Phone 8," Microsoft 2013 [online]. Feb. 1, 2013. Retrieved from the Internet: <http://msdn.microsoft.com/en-us/library/windowsphone/develop/jj206959(v=vs.105).aspx> 10 pgs.

(Continued)

*Primary Examiner* — Steve Rowland
(74) *Attorney, Agent, or Firm* — Shumaker & Sieffert, P.A.

(57) ABSTRACT

An example method includes obtaining user consent to collect and make use of personal information for providing behavioral coaching; obtaining contextual and fitness related information of a user; determining, by inputting the contextual and fitness related information into a model that defines a motivational state, a current motivational state of the user; determining, based at least in part on the current motivational state of the user, a type of information to output as part of the behavioral coaching, wherein the type of information is selected from a group comprising education information, inspirational information, and achievement information; determining, based on the type of information to output, a channel for outputting the type of information as part of the behavioral coaching; and outputting, by the computing device, via the channel, a notification including content of the type of information.

14 Claims, 10 Drawing Sheets

(56) References Cited

U.S. PATENT DOCUMENTS

| | | |
|---|---|---|
| 7,292,986 B1 | 11/2007 | Venolia et al. |
| 7,966,188 B2 | 6/2011 | Ativanichayaphong et al. |
| 8,275,617 B1 | 9/2012 | Morgan et al. |
| 8,328,612 B1 | 12/2012 | Ansari et al. |
| 9,990,177 B2 | 6/2018 | Faaborg et al. |
| 2005/0165609 A1 | 7/2005 | Zuberec et al. |
| 2006/0228681 A1* | 10/2006 | Clarke .................. G16H 20/30 434/236 |
| 2006/0264730 A1* | 11/2006 | Stivoric ............... A61B 5/7282 600/587 |
| 2007/0033054 A1 | 2/2007 | Snitkovskiy et al. |
| 2007/0061148 A1 | 3/2007 | Cross, Jr. et al. |
| 2007/0088557 A1 | 4/2007 | Andrew |
| 2007/0282176 A1* | 12/2007 | Shimada ................ G16H 40/63 600/300 |
| 2008/0215240 A1 | 9/2008 | Howard et al. |
| 2009/0009320 A1 | 1/2009 | O'Connor et al. |
| 2010/0257554 A1 | 10/2010 | Friedlander et al. |
| 2010/0312547 A1 | 12/2010 | Van Os et al. |
| 2011/0013756 A1 | 1/2011 | Davies et al. |
| 2011/0301955 A1 | 12/2011 | Byrne et al. |
| 2012/0010809 A1 | 1/2012 | Stut et al. |
| 2012/0110456 A1 | 5/2012 | Larco et al. |
| 2012/0253822 A1 | 10/2012 | Schalk |
| 2012/0253824 A1 | 10/2012 | Alcantara Talavera |
| 2013/0018656 A1 | 1/2013 | White et al. |
| 2013/0080178 A1 | 3/2013 | Kang et al. |
| 2013/0110508 A1 | 5/2013 | Bak et al. |
| 2013/0116092 A1* | 5/2013 | Martinez ............ A63B 24/0062 482/9 |
| 2013/0211836 A1 | 8/2013 | Jordan et al. |
| 2013/0219277 A1 | 8/2013 | Wang et al. |
| 2013/0253937 A1 | 9/2013 | Cho et al. |
| 2014/0052567 A1 | 2/2014 | Bhardwaj et al. |
| 2014/0087336 A1* | 3/2014 | Wang .................... A61B 5/222 434/127 |
| 2014/0156645 A1* | 6/2014 | Brust ................... G06F 3/0481 707/722 |
| 2014/0207452 A1 | 7/2014 | Klein et al. |
| 2014/0213920 A1* | 7/2014 | Lee ....................... A61B 5/222 600/509 |
| 2014/0222436 A1 | 8/2014 | Binder et al. |
| 2014/0249379 A1* | 9/2014 | Proud .................. A61B 5/0022 600/301 |
| 2014/0278443 A1 | 9/2014 | Gunn et al. |
| 2014/0330094 A1* | 11/2014 | Pacione ................ A61B 5/165 600/300 |
| 2015/0040012 A1 | 5/2015 | Faaborg et al. |
| 2015/0261496 A1 | 9/2015 | Faaborg et al. |
| 2016/0074707 A1* | 3/2016 | Thorpe .............. G09B 19/0092 434/247 |
| 2016/0086509 A1* | 3/2016 | Petrov .................... G06Q 10/10 434/127 |
| 2016/0171180 A1* | 6/2016 | Yagnyamurthy ...... G16H 20/70 705/3 |
| 2017/0213470 A1* | 7/2017 | Briggs ............... G09B 19/0038 |
| 2019/0094372 A1* | 3/2019 | Graham ................ H04W 4/029 |
| 2020/0279500 A1* | 9/2020 | Petrov .................... G09B 19/00 |

FOREIGN PATENT DOCUMENTS

| | | |
|---|---|---|
| WO | 2014093856 A1 | 6/2014 |
| WO | 2015017043 A1 | 2/2015 |

OTHER PUBLICATIONS

Apple, "Moves—Let your iPhone tell you how much you move," Apple, 2014, Retrieved from the internet on Jun. 17, 2015, 3 pp.

Derek Walter, "Google buys Timeful, plans to inject its machine learning into its own apps," Green Bot by IDG Communications, May 4, 2015, 3 pp.

DeskActive, "Customize your account settings to personalize your experience," DeskActive, 2014, Retrieved on Jun. 17, 2015 from <http://www.deskactive.com/How-it-Works/Settings.aspx> 3 pp.

Endomondo, "Our Concept," Endomondo, Retrieved on Jun. 17, 2015, from <https://www.endomondo.com/history> 3 pp.

"Gmail, ""Time is on your side—welcoming Timeful to Google,"" Official Gmail Blog, May 4, 2015, Retrieved from http://gmailblog.blogspot.com/2015/05/timeisonyoursidewelcomingtimeful.html> 2 pp."

Google Inc., "Google Fit," Android Apps on Google Play, May 14, 2015, Retrieved from <https://playgoogle.com/store/apps/details?id=com.google.android.apps.fitness&hl=en> 2 pp.

Google Play, "Apps by Kickstand Technology LLC," Google Play, 2013, 1 pp.

JCP Innovations, "Cycle Weather," Google Play, Apr. 2, 2013, 1 pp.

The Greatist Team, "The 64 Best Health and Fitness Apps of 2013," Greatist, Mar. 27, 2013, Retrieved from <http://greatist.com/fitness/best-health-fitness-apps-2013> 36 pp.

* cited by examiner

FRAMEWORK FOR A COMPUTING SYSTEM THAT ALTERS USER BEHAVIOR

This application claims the benefit of U.S. Provisional Application No. 62/720,692, filed Aug. 21, 2018, the entire content of which is hereby incorporated by reference.

BACKGROUND

To help users to maintain more healthy and active lifestyles, various types of mobile and wearable devices exist for tracking user activity and/or providing status indicators throughout the day as users work toward achieving fitness goals. While these types of devices may be well suited for recording exercise statistics and physiological data, e.g., so a user can track whether they are progressing towards achieving a fitness goal, the user may still not be aware of how to achieve the fitness goal.

SUMMARY

In general, techniques of this disclosure may enable a computing system to provide personalized, and contextually relevant output that alters user behavior for assisting a user in achieving a behavioral goal. Such output may be conveyed to further a treatment plan, for example, prescribed by a practitioner (e.g., physician, dietitian, etc.) to treat obesity, heart disease, or other medical ailment. For instance, in the fitness context, the described techniques may enable a mobile phone or computerized watch to display notifications that motivate and coach a user to take certain physical or dietary actions that will help the user to achieve a desired fitness goal, such as losing weight. The described techniques work off a model or framework, which maps a plurality of motivational states to a plurality of possible different contexts of a user. Each motivational state specifies one or more types of information, and one or more ways to present each type of information, to have a better chance at inducing actual behavioral changes, e.g., in furtherance of a treatment plan. When the example computing system outputs information for motivating or coaching the user, the model causes the computing system to output the information according to a current motivational state. The model outputs information to cause a change in a user's context and further cause transition to a subsequent motivational state of the model. The example computing system outputs information in this way to induce user actions that enable the model to cycle through each of the different motivational states, e.g., to achieve a treatment plan. By adapting how motivational information is output for different motivational states and different contexts, an example computing system may be far more likely to gain positive attention from a user and therefore may be more likely to induce behavioral change in furtherance of a treatment plan, more so than other computing systems that merely provide tracking or status indicators. In this way, the techniques As such, rather than be a distraction or waste battery power providing intrusive and often annoying alerts, the example computing system provides targeted, contextually accurate, and personalized output that is aesthetically pleasing and achieves behavioral change to help a user achieve a treatment plan.

Throughout the disclosure, examples are described where a computing device and/or computing system may analyze information (e.g., contextual information, user and/or device data, etc.). However, the system may only use the information after the computing device and/or the computing system receives explicit permission from a user of the computing device and/or the computing system. For example, in situations discussed below in which the computing device and/or computing system may collect information about user interactions with applications executing at computing devices or computing systems, individual users may be provided with an opportunity to provide input to control whether programs or features of the computing device and/or computing system can collect and make use of the information. The individual users may further be provided with an opportunity to control what the programs or features can or cannot do with the information.

In addition, information collected may be pre-treated in one or more ways before it is transferred, stored, or otherwise used by a computing device and/or computing system, so that personally-identifiable information is removed. For example, before an example computing system stores user interaction data associated with an application executing at a computing device, the example computing system may pre-treat the data to ensure that any user identifying information or device identifying information embedded in the data is removed. Thus, the user may have control over whether information is collected about the user and user's device, and how such information, if collected, may be used by the computing device and/or computing system.

The details of one or more examples are set forth in the accompanying drawings and the description below. Other features, objects, and advantages of the disclosure will be apparent from the description and drawings, and from the claims.

DETAILED DESCRIPTION

Figure 1:
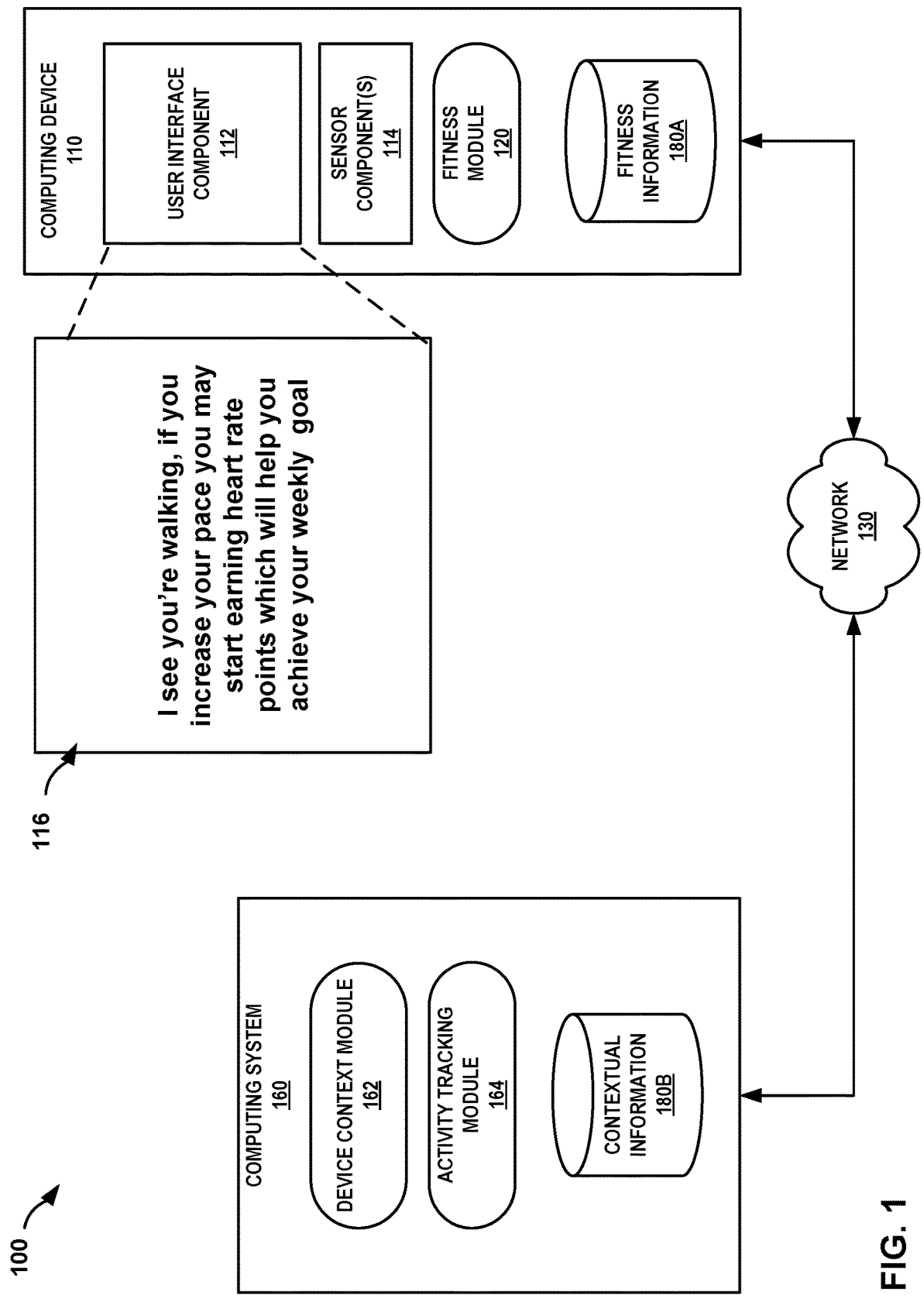
FIG. 1 is a conceptual diagram illustrating an example system configured to provide personalized, and contextually relevant output that alters user behavior for assisting a user in achieving a behavioral goal, in accordance with one or more aspects of the present disclosure.

FIG. 1 is a conceptual diagram illustrating an example system configured to provide personalized, and contextually relevant output that alters user behavior for assisting a user in achieving a behavioral goal, in accordance with one or more aspects of the present disclosure. System 100 of FIG. 1 includes computing device 110 and computing system 160 communicatively coupled to network 130. Although operations attributed to system 100 are described primarily as being performed by computing system 160 and computing device 110, in some examples, the operations of system 100 may be performed by additional or fewer computing devices and systems than what is shown in FIG. 1. For example, computing device 110 may include some or all of the functionality of computing system 160, or vice versa.

Network 130 represents any public or private communications network for transmitting data between computing systems, servers, and computing devices. Network 130 may be a public switched telephone network (PSTN), a wireless network (e.g., cellular, Wi-Fi®, and/or other wireless network), a wired network (e.g., a local area network (LAN), a wide area network (WAN), the Internet, etc.), an Internet Protocol (IP) telephony network, such as voice-over-IP (VoIP) network, or any other type of communications network. Network 130 may include one or more network hubs, network switches, network routers, or any other network equipment, that are operatively inter-coupled thereby providing for the exchange of information between computing system 160 and computing device 110. Computing system 160 and computing device 110 may transmit and receive data across network 130 using any suitable communication techniques.

Computing system 160 and computing device 110 may each be operatively coupled to network 130 using respective network links. The links coupling computing system 160 and computing device 110 to network 130 may be Ethernet, or other types of network connections, and such connections may be wireless and/or wired connections.

In the example of system 100, computing system 160 provides supplemental information to computing device 110 that supports the model or frame work implemented by computing device 110 to induce user behavioral change. Computing system 160 represents any combination of one or more computers, mainframes, servers (including so-called "blades"), cloud computing systems, or other types of remote computing systems capable of exchanging information via network 130. Computing system 160 may provide a service from which computing device 110 may obtain the supplemental information that enables computing device 110 to implement a motivational model or framework that maps a plurality of motivational states to a plurality of possible different contexts of a user of computing device 110. Examples of supplemental information include contextual information as well as activity tracking information.

Computing device 110 represents any suitable computing device or computing system capable of exchanging information via network 130 to implement a motivational model or framework for inducing user behavioral change. For example, computing device 110 may be a mobile device, such as a computerized watch or mobile telephone, that a user wears or carries during a workout. Examples of computing device 110 include mobile phones, tablet computers, laptop computers, desktop computers, servers, mainframes, wearable devices (e.g., computerized watches, hearables, etc.), home automation devices, assistant devices, gaming consoles and systems, media players, e-book readers, television platforms, automobile navigation or infotainment systems, or any other type of mobile, non-mobile, wearable, and non-wearable computing devices configured to exchange information via a network, such as network 130.

Computing system 160 includes device context module 162, activity tracking module 164, and contextual information data store 180B. Modules 162 and 164 may perform operations described using software, hardware, firmware, or a mixture of hardware, software, and firmware residing in and/or executing at computing system 160. Computing system 160 may execute information modules 162 and 164 with multiple processors or multiple devices. Computing system 60 may execute modules 162 and 164 as a virtual machine executing on underlying hardware. Modules 162 and 164 may execute as a service of an operating system or computing platform. Modules 162 and 164 may execute as one or more executable programs at an application layer of a computing platform.

Device context module 162 may process and analyze contextual information associated with computing device 110. In some cases, device context module 162 may process contextual information to define a context of computing device 110 or a context of a user of computing device 110. Data store 180B represents any suitable storage medium for contextual information minted by device context module 162. Device context module 162 may collect contextual information associated with computing device 110, and store the collected contextual information at data store 180B.

As used throughout the disclosure, the term "contextual information" refers to any conceivable information that may be used by a computing system and/or computing device, such as computing device 110, to implement a motivational model or framework for inducing user behavioral change. Contextual information may include: device location and/or sensory information, user topics of interest (e.g., a user's favorite "things" typically maintained as a user interest graph or some other type of data structure), contact information associated with users (e.g., a user's personal contact information as well as information about a user's friends, co-workers, social media connections, family, etc.), search histories, location histories, long-term and short-term tasks, calendar information, application usage histories, purchase histories, items marked as favorites, electronic bookmarks, and other information that computing device 110 and computing system 160 can gather about a user of computing device 110 from interactions with computing device 110.

Furthermore, contextual information may include information about the operating state of a computing device. For example, an application that is executed at a given time or in a particular location is an example of information about the operating state of a computing device. Other examples of contextual information that is indicative of an operating state of a computing device include, but are not limited to, positions of switches, battery levels, whether a device is plugged into a wall outlet or otherwise operably coupled to another device and/or machine, user authentication information (e.g., which user is currently authenticated-on or is the current user of the device), whether a device is operating in "airplane" mode, in standby mode, in full-power mode, the operational state of radios, communication units, input devices and output devices, etc.

In contrast to "contextual information" the term "context" refers to a particular state of each characteristic from a collection of characteristics associated with a computing device and/or a user of a computing device, at a particular time. The context may indicate characteristics associated with the physical and/or virtual environment of the user and/or the computing device at a particular location and/or time. As some examples, a context of a computing device may specify an acoustic fingerprint, a video fingerprint, a location, a movement trajectory, a direction, a speed, a name of a place, a street address, a type of place, a building, weather conditions, and traffic conditions, at various locations and times. As some additional examples, the context of a computing device may specify a calendar event, a meeting, or other event associated with a location or time.

In some examples, a context of a computing device may specify any application, or webpage accessed at a particular time, one or more text entries made in data fields of the webpages at particular times, including search or browsing histories, product purchases made at particular times, product wish lists, product registries, and other application usage data associated with various locations and times. The context of the computing device may further specify audio and/or video accessed by or being broadcast in the presence of the computing device at various locations and times, television or cable/satellite broadcasts accessed by or being broadcast in the presence the computing device at various locations and times, and information about other services accessed by the computing device at various locations and times.

When collecting, storing, and using contextual information or any other user or device data, computing system 160 and computing device 110 take precautions to ensure that user privacy is preserved. Computing device 110 and computing system 160 may only collect, store, and analyze contextual information if computing device 110 and computing system 160 receive explicit permission of individual users from which the contextual information originates. For example, in situations in which computing device 110 may collect information about a user, a user of computing device 110 may be provided with an opportunity to provide input to computing device 110 to control whether computing device 110 can collect and make use of their information. The individual users may further be provided with an opportunity to control what computing device 110 can or cannot do with the information.

Any data being collected by computing device 110 and computing system 160 may be pre-treated in one or more ways before it is transferred to, stored by, or otherwise used by computing device 110 and computing system 160, so that personally-identifiable information is removed. For example, before computing device 110 and computing system 160 collects contextual information computing device 110 and computing system 160 may pre-treat the contextual information to ensure that any user identifying information or device identifying information embedded in the contextual information is removed before being stored by computing device 110 and computing system 160. The user has complete control over whether contextual information is collected, and if so, how such information may be used by computing device 110 and computing system 160.

Activity tracking module 164 may determine, based on contextual information, one or more activities being performed by a user at a particular time. For example, activity tracking module 164 may execute a rules-based algorithm or a machine learning system that predicts, based on a current context, what a user of a computing device is doing at a given time. The rules based algorithm or machine learning system may be based on various observations about user behavior for different contexts.

Activity tracking module 164 may query device context module 162 for an indication of a context associated with a user of computing device 110 and responsive to inputting the context into a rules-based algorithm or a machine learning system, receive an output indicative of one or more activities that the user may be performing given the context. For example, if a context received from device context module 162 defines a speed and a location of computing device 110 that coincides with the speed of typical train when the train moves on a particular rail track, then the system may predict, based on the rules, that the user is a passenger of a particular train. In other examples, if the context received from device context module 162 indicates that the location of computing device 110 corresponds to a work location of a user and that the location has not changed for some period of time, the system may predict, based on the rules, that the user is likely sitting or standing at his or her work desk. In still other examples, if the context received from device context module 162 indicates that the location of computing device 110 corresponds to bus stop of a bus line that the user normally takes to go home at the current time, the system may predict, based on the rules, that the user is likely waiting for a bus to return home.

In some examples, activity tracking module 164 may determine a respective score, probability, or other degree of likelihood associated with each of the one or more activities that indicates how likely or unlikely that the user is actually performing the activity for the particular time. For instance, activity tracking module 164 may determine with a contextually dependent confidence score that a user is driving a car, riding in a train, sitting at a desk, or performing some other activity.

Activity tracking module 164 may provide an application programming interface (API) from which computing devices, such as computing device 110, can query activity tracking module 164 for a current activity being performed by a user at a particular time. For example, responsive to receiving a query, through network 130, from computing device 110 of the current activity being performed by the user of computing device 110, activity tracking module 164 may output, via network 130, an indication (e.g., data, a message, a signal) that indicates which activity the user is likely performing at the current time and/or a probability, score, or other degree of likelihood or confidence level that the system has that the user is performing the activity. For example, activity tracking module 164 may respond to a query from computing device 110 with a message indicating that the system predicts, with a high degree of confidence, the user is watching television, waiting at a bus stop, sleeping, eating, working, or some other activity.

As shown in FIG. 1, computing device 110 includes user interface component (UIC) 112 which is configured to output user interface 116. UIC 112 of computing device 110 may function as an input and/or output device for computing device 110. UIC 112 may be implemented using various technologies. For instance, UIC 112 may function as an input device using presence-sensitive input screens, microphone technologies, infrared sensor technologies, or other input device technology for use in receiving user input. UIC 112 may function as output device configured to present output to a user using any one or more display devices, speaker technologies, haptic feedback technologies, or other output device technology for use in outputting information to a user. UIC 112 may be used by computing device 110 to output, for display, a GUI, such as user interface 116.

Computing device 110 also includes one or more sensor components 114. Numerous examples of sensor components 114 exist and include any input component configured to obtain environmental information about the circumstances surrounding computing device 110 and/or physiological information that defines the activity state and/or physical well-being of a user of computing device 110. For example, sensor components 114 may include movement sensors (e.g., accelerometers), temperature sensors, position sensors (e.g., a gyro), pressure sensors (e.g., a barometer), proximity sensors (e.g., an inferred sensor), ambient light detectors, heart-rate monitors, blood pressure monitors, blood glucose monitors, and any other type of sensing component. Computing device 110 may use sensor components 114 to obtain contextual information associated with computing device 110 and a user. In some examples, computing device 110 may rely on the sensor information obtained by sensor components 114 to execute operations locally on-device. Whereas in some examples, computing device 110 may relay information obtained from sensor components 114 to computing system 160 (e.g., for storage and subsequent processing at data store 180B).

Computing device 110 includes fitness information data store 180A which represents any suitable storage medium for storing data, specifically, data related to fitness information. In general, the term "fitness information" refers to any information that computing device 110 may use to determine a recommended physical activity that a person may perform, for a particular context (e.g., to achieve a fitness goal). Examples of fitness goals include a user's gender, a user's age, a maximum or minimum heart rate level, a maximum or minimum amount of time spent sitting down or otherwise remaining sedentary, a body weight, a quantity of footsteps taken by a person over a time duration, a distance traveled over a time duration, and/or an amount of time spent by a person performing a physical activity or exercise.

The fitness information stored at data store 180A may be generic information (e.g., normalized across multiple people) and/or may be specific information associated with particular person, such as a user of computing device 110. For example, computing device 110 may store information related to one or more fitness goals associated with averaged users of multiple computing devices, including computing device 110; and computing device 110 may store information related to one or more fitness goals associated with a particular user of computing device 110. As described below, fitness module 120 may access the fitness information data stored at data store 180A.

Although data store 180A may contain fitness information associated with individual users, the information may be treated such that all personally-identifiable-information (such as name, address, telephone number, e-mail address) linking the information back to individual people may be removed before being stored at computing device 110. In addition, computing device 110 may only store fitness information associated with users of computing device 110 if those users affirmatively consent to such collection of information. Computing device 110 may further provide opportunities for users to remove such consent and in which case, computing device 110 may cease collecting fitness and contextual information associated with that particular user.

Fitness information data store 180A may store information related to one or more types of physical activities or exercises (e.g., bicycling, walking, running, jogging, canoeing, kayaking, roller skating) that a person may perform in order to be more physically active at a particular time. For example, fitness information data store 180A may store fitness information about bicycle riding, such as an average amount of energy expended by a person per unit of distance traveled while the person rides a bicycle. Other examples of fitness information may include weather information (e.g., temperature, humidity) indicative of a stated and/or predicted preferred weather condition that a person prefers while walking. In some examples, fitness information data store 180A may store types of physical activities or exercises according to pre-defined contexts. For example, fitness information data store 180A may include a matrix of different contexts and corresponding activities. A row of the matrix may be associated with a particular context and each column may be associated with a particular activity. Accordingly, the matrix may define, for each of the different context, which types of activities that could be performed, in those different contexts.

Other examples of the types of information stored at data store 180A include information about a person's stated or inferred fitness goals, workout history, current exercise performance, historical fitness performance or historical activity information (e.g., average walking speed, jogging speed, heart rates, etc.). Still other types of information stored at data store 180A may include information that indicates a person's daily activity level for a current day, current month, current year, or a history of the person's daily activity levels over multiple days, months, or years. For example, data store 180A may include an entry that indicates a quantity of steps taken by the user for the current day or a projected quantity of calories burned by the user on the particular day.

The fitness information may be organized and searchable within data store 180A (e.g., according to physical activity or exercise type, individual person's names, etc.). Computing device 110 may access the data within data store 180A, for instance, by executing a query command related to one or more potential physical activities that could be performed for a particular context. Responsive to the query command, computing system 160 may obtain information from data store 180A related to the one or more recommended physical activities from the one or more potential physical activities that best fit a user's lifestyle or preferred exercising habits that computing device 110 infers from the fitness information in data store 180A, or the one or more recommended physical activities that may otherwise assists the user in achieving his or her fitness goals (e.g., for becoming more active). Computing device 110 may use the information retrieved from data store 180A to determine whether or not to recommend a particular physical activity as a recommended physical activity for a user of computing device 110 to perform at the current time.

Computing device 110 includes fitness module 120. Fitness module 120 provides personalized, and contextually relevant output that alters behaviors of a user for assisting the user in achieving a behavioral goal, e.g., as part of a treatment plan from a coach, physician, nurse, etc. Fitness module 120 may perform operations described using software, hardware, firmware, or a mixture of hardware, software, and firmware residing in and/or executing at computing device 110. Computing device 110 may execute fitness module 120 with one or more processors. Computing device 110 may execute fitness module 120 as a virtual machine executing on underlying hardware. Fitness module 120 may execute as a service or component of an operating system or computing platform. Fitness module 120 may execute as one or more executable programs at an application layer of a computing platform.

Fitness module 120 may cause UIC 112 to present a graphical user interface from which a user can monitor, track, and be apprised of behavioral altering information determined by fitness module 120 to help a user achieve a behavioral goal. For instance, user interface 116 shows an example of the type of graphical user interface that fitness module 120 may cause UIC 112 to display for alerting or notifying a user about fitness related information. In the example of FIG. 1, user interface 116 illustrates a notification or an "information card" as one example graphical element that fitness module 120 may present at UIC 112. These so-called information cards may present fitness information that is relevant for a current context of computing device 110. Fitness module 120 may cause UIC 112 to present an information card, for instance, in response to determining that the user would like to be nudged into performing an exercise at the current time.

Fitness module 120 provides personalized, and contextually relevant output that alters user behavior for assisting a user in achieving a behavioral goal by relying on a model or framework. The model or framework maps a plurality of motivational states to a plurality of possible different contexts of a user. Each motivational state specifies one or more types of information, and one or more ways to present each type of information, to have a better chance at inducing actual behavioral changes, e.g., in furtherance of a treatment plan.

Fitness module 120 may rely on the model to determine a current motivational state of a user. The motivational state may be selected by the model from a plurality of different motivational states. As one example, the plurality of motivational states may include a preparation state, an action state, a maintenance state, and a regression state. Each of the states is described in greater detail below with respect to the additional FIGS. The model may analyze contextual information and fitness information maintained at data stores 180A and 180B to determine whether the contextual and fitness information satisfies rules embedded in the model that stipulate when to transition from one motivational state to the next. Each cycle through the different motivational states corresponds to an achievement, e.g., a fitness goal, a fitness milestone, a behavioral change, a physiological state, etc. Hence, after completing a cycle through the different motivational states, the model may initiate a subsequent cycle through the different motivational states, so as to accomplish a more challenging behavioral change or achievement.

Depending on the current motivational state of a user, fitness module 120 selects information to output to a user and a particular way to output the information, to induce behavioral changes that cause a transition in the model from a current motivational state to a subsequent motivational state. For example, in a preparation state, fitness module 120 may initially select educational information to teach a user how to achieve a particular behavioral change and present the educational information in a way that suits a current context. Whereas in an action or maintenance state, fitness module 120 may initially select motivational information to encourage a user how to keep working towards or maintaining a particular behavioral change and present the motivational information in a way that suits the current context.

Over time, by causing a computing device to output more personalized and targeted messages to coach a user towards a particular behavioral change, the described techniques may enable the computing device to coach a user into becoming more physically active. Such coaching may in some instances be part of a treatment plan, e.g., as prescribed by a medical professional to treat obesity, diabetes, heart disease and the like. Moreover, the described techniques may enable a computing device to perform these operations automatically without, for example, requiring such operations be initiated by the user thereby reducing the amount of user input, effort, and time required for figuring out how to complete a prescribed treatment plan. By not requiring the user to provide input to track fitness progress and set up alerts for becoming active, the computing device may perform fewer operations related to receiving the user input and therefore, consume less electrical power, which may result in longer battery life.

Figure 2:
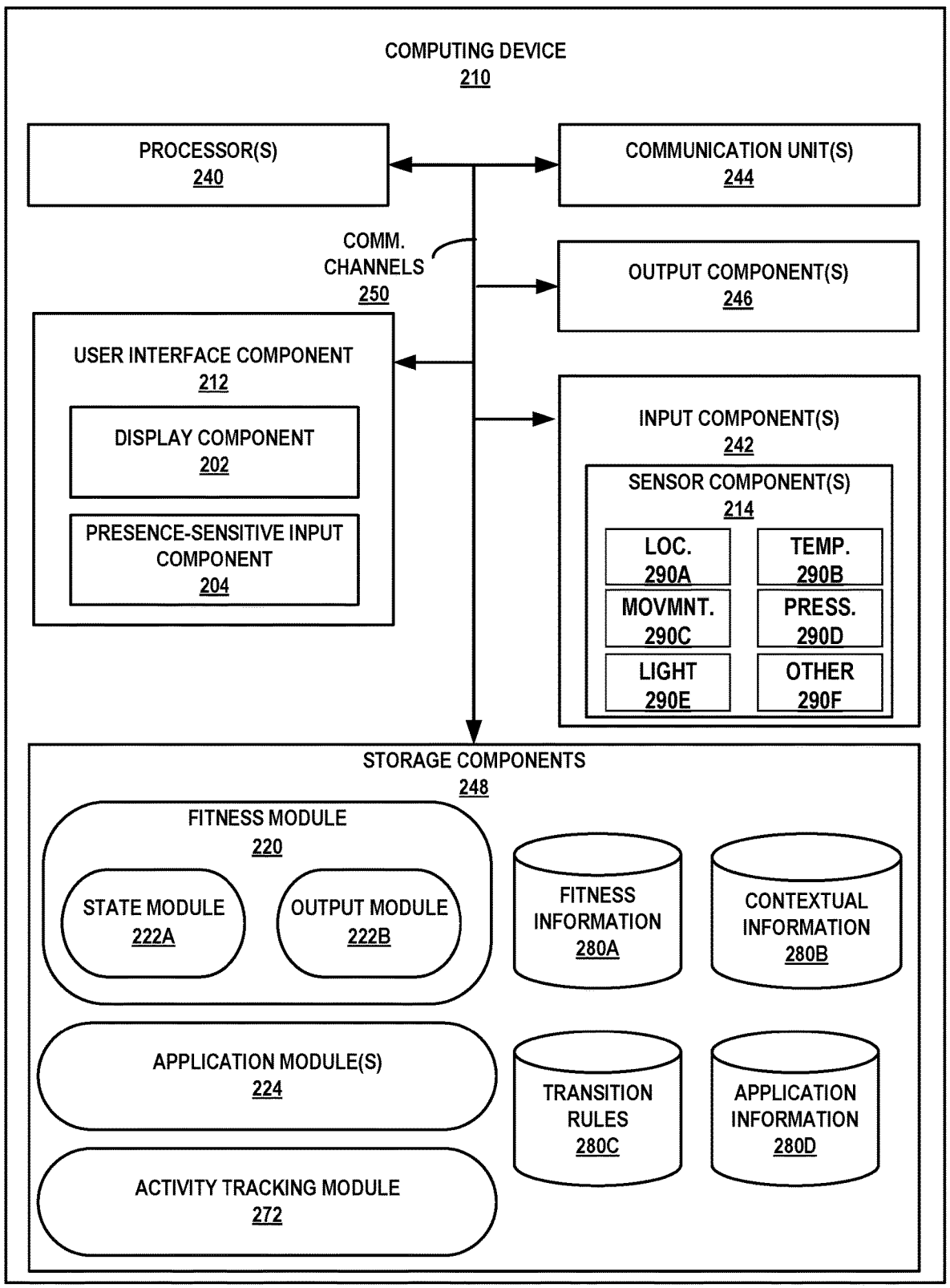
FIG. 2 is a block diagram illustrating an example computing device configured to provide personalized, and contextually relevant output that alters user behavior for assisting a user in achieving a behavioral goal, in accordance with one or more aspects of the present disclosure.

FIG. 2 is a block diagram illustrating an example computing device configured to provide personalized, and contextually relevant output that alters user behavior for assisting a user in achieving a behavioral goal, in accordance with one or more aspects of the present disclosure. Computing device 210 of FIG. 2 is an example of computing device 110 and described below within the context of system 100 of FIG. 1. Computing device 210 may include some or all of the capability of system 100 of FIG. 1. FIG. 2 illustrates only one particular example of computing device 210, and many other examples of computing device 210 may be used in other instances and may include a subset of the components included in example computing device 210 or may include additional components not shown in FIG. 2.

As shown in the example of FIG. 2, computing device 210 includes user interface component (UIC) 212, one or more processors 240, one or more input components 242, one or more communication units 244, one or more output components 246, and one or more storage components 248. UIC 212 includes display component 202 and presence-sensitive input component 204. Input components 242 include sensor components 214.

Storage components 248 of computing device 210 also includes fitness module 220, one or more application modules 224, and activity tracking module 272. Fitness module 220 also includes state module 222A and output module 222B. Additionally, storage components 248 include fitness information data store 280A, contextual information data store 280B, transition rules data store 280C, and application information data store 280D (which exists either as a separate data store or as a subset of contextual information data store 280B). Collectively, data stores 280A-280D may be referred to as "data stores 280".

Communication channels 250 may interconnect each of the components 202, 204, 212, 214, 220, 222A, 22B, 224, 272, 240, 242, 244, 246, 248, and 280 for inter-component communications (physically, communicatively, and/or operatively). In some examples, communication channels 250 may include a system bus, a network connection, an inter-process communication data structure, or any other method for communicating data.

One or more input components 242 of computing device 210 may receive input. Examples of input are tactile, audio, and video input. Input components 242 of computing device 200, in one example, includes a presence-sensitive display, touch-sensitive screen, mouse, keyboard, voice responsive system, video camera, microphone or any other type of device for detecting input from a human or machine. One or more input components 242 include one or more sensor components 214. Numerous examples of sensor components 214 exist and include any input component configured to obtain environmental information about the circumstances surrounding computing device 210 and/or physiological information that defines the activity state and/or physical well-being of a user of computing device 210. For instance, sensor components 214 may include one or more location sensors 290A (GPS components, Wi-Fi components, cellular components), one or more temperature sensors 290B, one or more movement sensors 290C (e.g., accelerometers, gyros), one or more pressure sensors 290D (e.g., barometer), one or more ambient light sensors 290E, and one or more other sensors 290F (e.g., microphone, camera, infrared proximity sensor, hygrometer, and the like).

One or more output components 246 of computing device 210 may generate output. Examples of output are tactile, audio, and video output. Output components 246 of computing device 210, in one example, includes a presence-sensitive display, sound card, video graphics adapter card, speaker, cathode ray tube (CRT) monitor, liquid crystal display (LCD), or any other type of device for generating output to a human or machine.

One or more communication units 244 of computing device 210 may communicate with external devices via one or more wired and/or wireless networks by transmitting and/or receiving network signals on the one or more networks. Examples of communication unit 244 include a network interface card (e.g. such as an Ethernet card), an optical transceiver, a radio frequency transceiver, a GPS receiver, or any other type of device that can send and/or receive information. Other examples of communication units 244 may include short wave radios, cellular data radios, wireless network radios, as well as universal serial bus (USB) controllers.

UIC 212 of computing device 200 includes display component 202 and presence-sensitive input component 204. Display component 202 may be a screen at which information is displayed by UIC 212 and presence-sensitive input component 204 may detect an object at and/or near display component 202. As one example range, presence-sensitive input component 204 may detect an object, such as a finger or stylus that is within two inches or less of display component 202. Presence-sensitive input component 204 may determine a location (e.g., an (x,y) coordinate) of display component 202 at which the object was detected. In another example range, presence-sensitive input component 204 may detect an object six inches or less from display component 202 and other ranges are also possible. Presence-sensitive input component 204 may determine the location of display component 202 selected by a user's finger using capacitive, inductive, and/or optical recognition techniques. In some examples, presence-sensitive input component 204 also provides output to a user using tactile, audio, or video stimuli as described with respect to display component 202. In the example of FIG. 2, UIC 212 presents a user interface (such as user interface 116 of FIG. 1).

While illustrated as an internal component of computing device 210, UIC 212 may also represent and external component that shares a data path with computing device 210 for transmitting and/or receiving input and output. For instance, in one example, UIC 212 represents a built-in component of computing device 210 located within and physically connected to the external packaging of computing device 210 (e.g., a screen on a mobile phone). In another example, UIC 212 represents an external component of computing device 210 located outside and physically separated from the packaging of computing device 210 (e.g., a monitor, a projector, etc. that shares a wired and/or wireless data path with a tablet computer).

One or more processors 240 may implement functionality and/or execute instructions within computing device 210. For example, processors 240 on computing device 210 may receive and execute instructions stored by storage components 248 that execute the functionality of modules 220, 222A, 222B, 224, and 272. The instructions executed by processors 240 may cause computing device 210 to store information within storage components 248 during program execution. Examples of processors 240 include application processors, display controllers, sensor hubs, and any other hardware configure to function as a processing unit. Processors 240 may execute instructions of modules 220, 222A, 22B, 224, and 272 to cause UIC 212 to render portions of content of display data as one user interface screen shots at UIC 212. That is, modules 220, 222A, 222B, 224, and 272 may be operable by processors 240 to perform various actions or functions of computing device 210.

One or more storage components 248 within computing device 210 may store information for processing during operation of computing device 210 (e.g., computing device 210 may store data accessed by modules 220, 222A, 222B, 224, and 272 during execution at computing device 210). In some examples, storage component 248 is a temporary memory, meaning that a primary purpose of storage component 248 is not long-term storage. Storage components 248 on computing device 210 may be configured for short-term storage of information as volatile memory and therefore not retain stored contents if powered off. Examples of volatile memories include random access memories (RAM), dynamic random access memories (DRAM), static random access memories (SRAM), and other forms of volatile memories known in the art.

Storage components 248, in some examples, also include one or more computer-readable storage media. Storage components 248 may be configured to store larger amounts of information than volatile memory. Storage components 248 may further be configured for long-term storage of information as non-volatile memory space and retain information after power on/off cycles. Examples of non-volatile memories include magnetic hard discs, optical discs, floppy discs, flash memories, or forms of electrically programmable memories (EPROM) or electrically erasable and programmable (EEPROM) memories. Storage components 248 may store program instructions and/or information (e.g., data) associated with modules 220, 222A, 222B, 224, and 272, as well as data stores 280.

Application modules 224 represent all the various individual applications and services executing at computing device 210. A user of computing device 210 may interact with an interface (e.g., a graphical user interface) associated with one or more application modules 224 to cause computing device 210 to perform a function. Numerous examples of application modules 224 may exist and include, a calendar application, a personal assistant or prediction engine, a search application, a map or navigation application, a transportation service application (e.g., a bus or train tracking application), a social media application, a game application, an e-mail application, a messaging application, an Internet browser application, or any and all other applications that may execute at computing device 210.

Application modules 224 may store application information at application information data store 280D for later retrieval and use in performing a function. For example, a calendar application of modules 224 may store an electronic calendar at data store 280D. Similarly, an e-mail application, messaging application, search application, transportation service application, or any other one of application modules 224 may store information or data for later retrieval at data store 280D.

With explicit permission from a user of computing device 210, modules 220, 222A, 222B, and 272 may have access to information stored at data store 280D. For example, as described below, fitness module 220 may access data store 280D for calendar information, communication information, transportation information, or any other application information stored at data store 280D to determine a current motivational state of a user of computing device 210. Said differently, fitness module 220 may use the application data (also referred to as "application information") stored at data store 280D as contextual information for determining a current motivational state of a user, and in some example, a recommended action for the user to take to help the user achieve a particular behavioral change or complete a treatment plan. As such, contextual information data store 280B may include application information data store 280D as part of data store 280B or as a separate component, such that contextual information associated with computing device 210 includes sensor data obtained from one or more sensors 214, application data obtained from one or more application module 224 executing at computing device 210, calendar information associated with the user of computing device 210, and any all other information obtained by computing device 210 that can assist fitness module 220 in recommending exercises to a user.

Activity tracking module 272 may determine, based on contextual information, one or more activities being performed by a user at a particular time. Activity tracking module 272 may perform similar operations as activity tracking module 164. In other words, activity tracking module 272 may execute a rules based algorithm or a machine learning system that predicts what a user of computing device 210 is doing at a given time. The rules based algorithm or a machine learning system may be based on various observations about user behavior for different contexts such that activity tracking module 272 outputs an indication (e.g., data) of the predicted activity for use by fitness module 220 in recommending activities a user may perform in furtherance of a behavioral change.

In other examples, activity tracking module 272 represents an Application Programming Interface (API) associated with activity tracking module 164 of computing system 160. Activity tracking module 272 may provide an interface for receiving input to activity tracking module 164, and providing output received from activity tracking module 164, to other modules, applications, and/or components executing at computing device 210. For example, activity tracking module 272 may receive, as input from fitness module 220, an identifier of computing device 210 and/or contextual information associated with computing device 210 and in response, query activity tracking module 164 for an indication of one or more activities likely being performed by a user of computing device 210 at a particular time. Activity tracking module 272 may output the indication of the one or more activities back to fitness module 220.

Fitness module 220 may provide similar functionality as fitness module 120, of computing device 110, shown in FIG. 1. That is, fitness module 220 may determine, based on contextual information stored at data store 280B as well as fitness information stored at data store 280A, whether a current motivational state of a user and output information in a way that encourages the user to continue to work to transition to the next motivational state in a behavioral change cycle.

Fitness module 220 includes state module 222A. State module 222A represents a framework or model of various motivational states. State module 222A receives as input, contextual information and fitness information from data stores 280A and 280B, applies one or more transition rules from data store 280C to the inputs. The one or more transition rules produce, as an output, an indication of a current motivational state of the user.

State module 222A maps a plurality of motivational states to a plurality of possible different contexts of a user. Each motivational state indicates to output module 222B, one or more types of information, and one or more ways to present each type of information, to have a better chance at inducing actual behavioral changes, e.g., in furtherance of a treatment plan.

Transition rules data store 280C may be based on various observations about user behavior for different contexts. Some of the rules stored at data store 280C may analyze the contextual inputs to state module 222A to determine whether any patterns or values in the contextual information satisfy any thresholds for transitioning to a subsequent motivational state. In other words, transition rules data store 280C may be based on observations of user behavior as the users work towards achieving a particular behavioral goal. One transition rule may specify a frequency of exercise that needs to occur before state module 222A will transition from a current motivational state to a subsequent motivational state. Another transition rule may specify a particular weight or physiological parameter that needs to occur before state module 222A will transition. Many other examples of transition rules exist.

Output module 222B outputs information for motivating or coaching the user based on a current motivational state of the user. State module 222A provides output module 222B with an indication of a current motivational state. Output module 222B then selects information to output that satisfies the requirements for the current motivational state. Output module 222B selects and present information that output module 222B predicts will induce a change in a user's context and therefore cause a transition to a subsequent motivational state. By outputting information that is likely to cause a user of computing device 210 to change his or her context and therefore transition to a subsequent motivational state, output module 222B enables fitness module 220 to encourage a user to adopt a particular lifestyle that helps the user achieve a behavioral change or complete a treatment plan.

Figure 3:
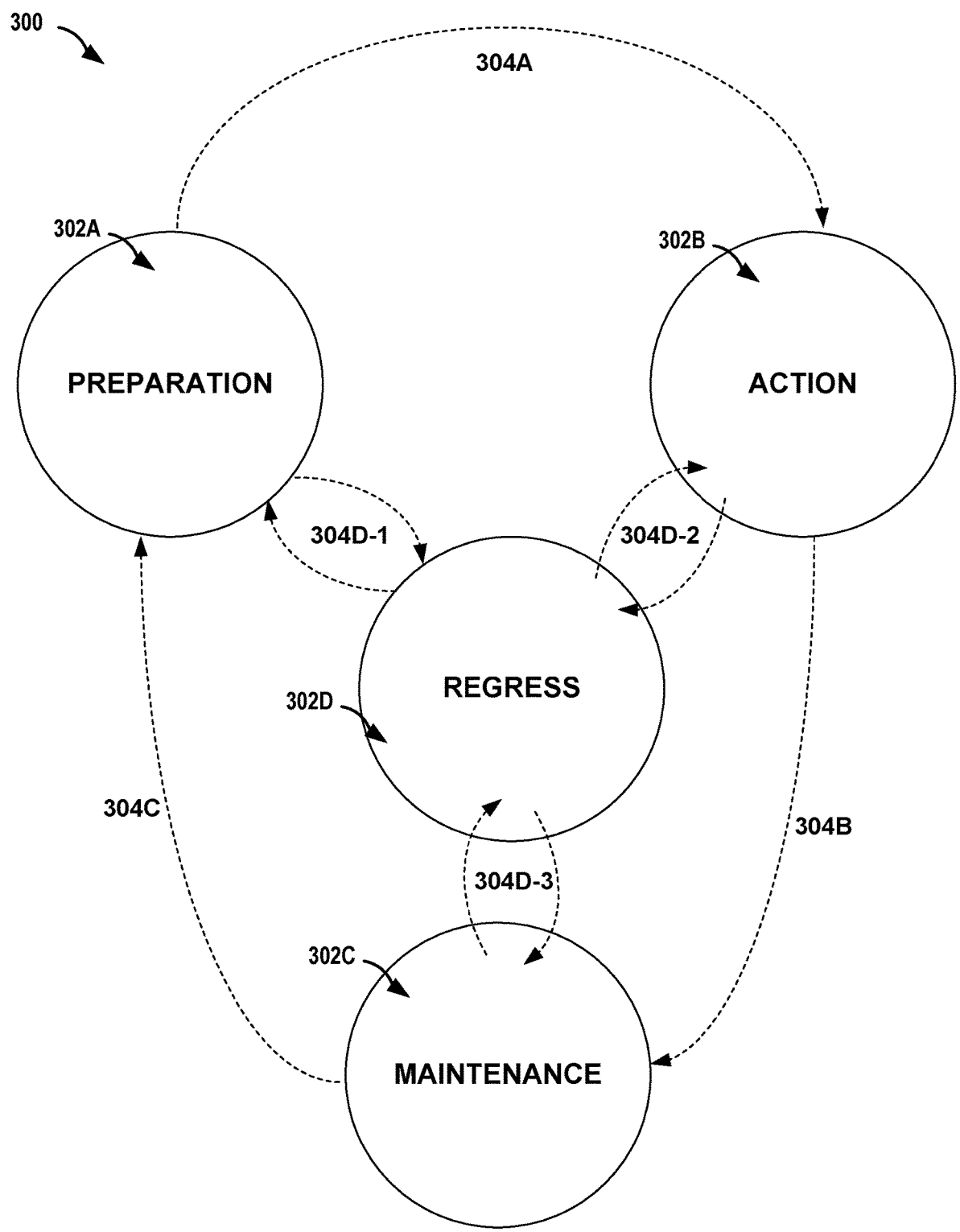
FIG. 3 is a state diagram illustrating an example computing model configured to map a plurality of motivational states to a plurality of possible different contexts of a user, in accordance with one or more techniques of the present disclosure.

FIG. 3 is a state diagram illustrating an example computing model configured to map a plurality of motivational states to a plurality of possible different contexts of a user, in accordance with one or more techniques of the present disclosure. FIG. 3 is described in the context of computing device 210 of FIG. 2. For example, state module 222A may perform operations that cause state module 222A to transition between the various states of state diagram 300 of FIG. 3.

State diagram 300 includes a plurality of motivational states 302A through 302D (collectively "plurality of motivational states 302" or "motivational states 302"). More or fewer motivational states may be used in some examples. In the example of FIG. 3, state diagram 300 includes preparation state 302A, action state 302B, maintenance state 302C, and regress state 302D. Each of the plurality of motivational states 302 related to each of the other motivational states 302 as defined by transition rules 304A, 304B, 304C, 304D-1, 304D-2, and 304D-1 (collectively "transition rules 304"). For example, to transition from preparation state 302A to action state 302B, state module 222B may require that the contextual information and/or fitness information associated with a user satisfy transition rules 304A or else remain in preparation state 302A.

State module 222A may operate under an assumption that there are many attributes of a user that are useful in providing a meaningful coaching experience to them. Alongside core characteristics like height and weight, state module 222A aims to account for max heart rate, average stride length as well as recent trends in user activity. Storing this type of data enables state module 222A to determine a user's motivational state which helps output module 222B to output information that coaches the user in ways which are most effective for inducing behavioral change and treatment.

As a working example, state module 222A may determine that a user context more closely maps to preparation state 302A when their activities, context, and fitness information indicate that a user would benefit from some education in how to accomplish a fitness goal and transition to a subsequent motivational state. In such an example, a user may have less than a threshold amount of active minutes a week.

State module 222A may determine that a user context more closely maps to action state 302B when their activities, context, and fitness information indicate that a user would benefit from some inspiration or motivation to continue to work towards accomplishing a fitness goal and transition to a subsequent motivational state. In such an example, a user may have achieved a threshold amount of active minutes a week for two or more weeks.

State module 222A may determine that a user context more closely maps to maintenance state 302C when their activities, context, and fitness information indicate that a user would benefit from a challenge to continue to work towards maintaining a fitness goal or to accomplish a new fitness goal, at which point state module 222A may transition to a subsequent motivational state. In such an example, a user may have achieved a threshold amount of active minutes a week for six or more weeks.

State module 222A is designed to account for relapses in treatment or behavioral change. That is, a relapse can happen at anytime and from any motivational states 302. As such, when state module 222A determines a user is in regress state 302D, state module 222A may identify specific behavioral changes a user can correct to transition back to a previous one of states 302. By identifying and providing preemptive coaching or timely motivation, state module 222A can help users avoid remaining in regress state 302D for too long so as to maintain healthy behavior. In such an example, a user may have missed achieving a threshold amount of active minutes a week for three or more weeks after previously having satisfied the criteria for being in one of preparation, action, or maintenance states (e.g., states 302). Other signs of regress include sudden or gradual activity level change, failure to achieve heart minute goals compared to history, manually reduces heart minute goal, workouts less frequently, or performance decreases.

Figure 4:
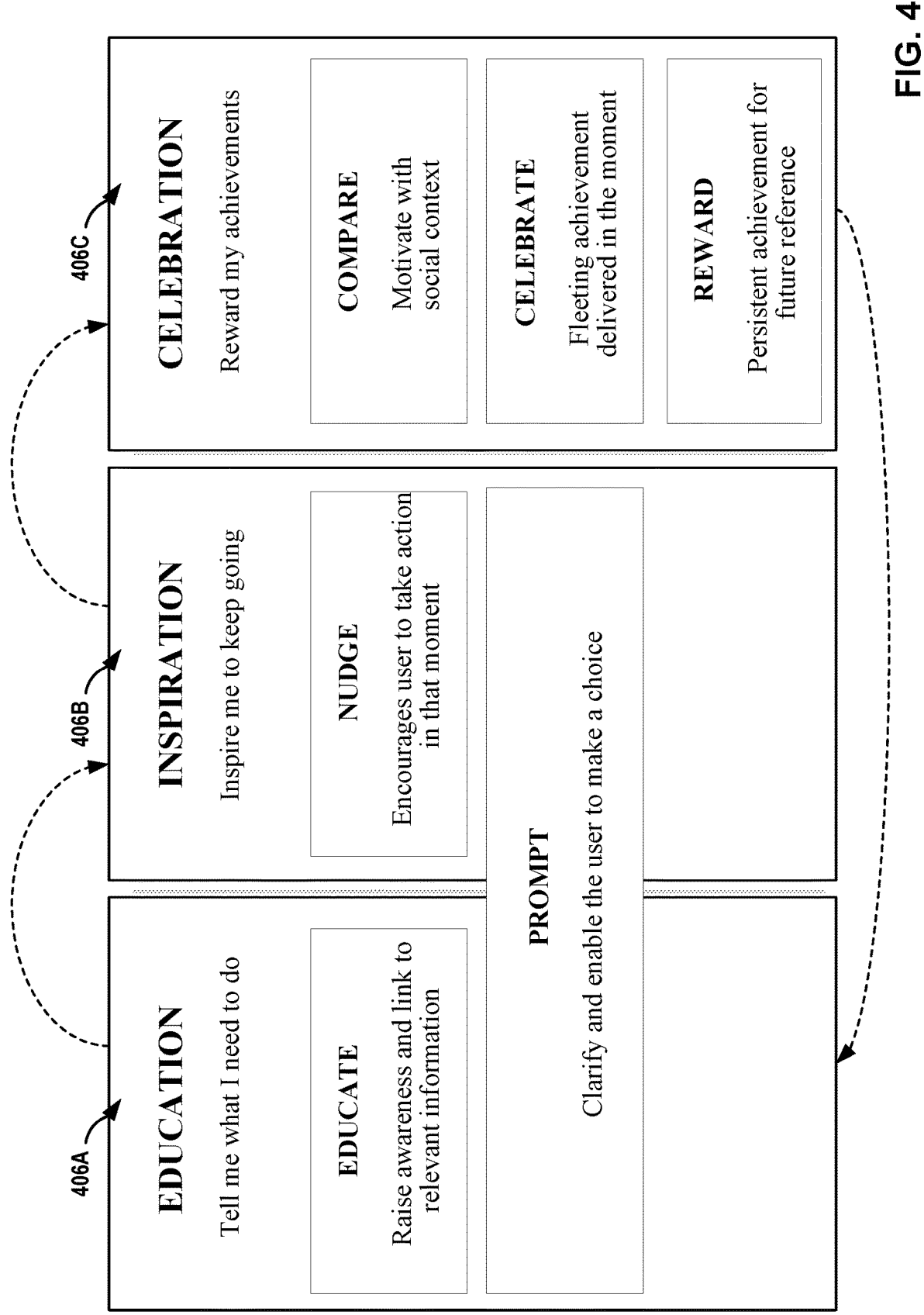
FIG. 4 is a conceptual diagram illustrating different types of information and ways to output the information, depending on a current motivational state of a user, in accordance with one or more techniques of the present disclosure.

FIG. 4 is a conceptual diagram illustrating different types of information and ways to output the information, depending on a current motivational state of a user, in accordance with one or more techniques of the present disclosure. FIG. 4 is described in the context of computing device 210 of FIG. 2 and state diagram 300 of FIG. 3.

Output module 222B is responsible for outputting information that will inspire a user, and is best suited to induce behavioral change, for a particular motivational state 302. That is, output module 222B may map an appropriate tone to output information, define a user interface pattern, identify where a coaching message should show up and when to trigger such a notification.

Output module 222B is based on three categories of information: education 406A, inspiration 406B, and celebration 406C (collectively "categories 406"). Each information type or category is associated with a particular format or tone. In this way, output module 222B is configured to output a particular category of information, and in a particular format, that best maps to a user's current motivational state 302. Said a different way, to succeed in motivating a user to adopt behavioral change, output module 222B does more than just output genericized or impersonal message triggers. Instead, output module 222B triggers the output of messages in the most opportune form and moment.

For example, when a user first transitions to preparation state 302A, output module 222A may initially output education 406A information to inform the user how to progress through preparation state 302A. Output module 222A may subsequently output inspiration 406B information to inform the user how as to any changes they may make to observed user behaviors to better progress through preparation state 302A. Output module 222A may finally output celebration 406C information to inform the user how as to any accomplishments that have occurred during the progress through preparation state 302A. Output module 222A may cycle through outputting information from each of categories 406 until contextual information or fitness information of a user satisfies transition rule 304A to progress to a subsequent motivation state 302. Similar operations may be performed by output module 222B to output information in each of categories 406 that helps the user advance through each motivational state 302. By helping the user advance through the motivational states, computing device 210 may effectively administer treatment in furtherance of a treatment plan. Furthermore, by using the contextual and fitness related information to determine advancement through the motivational states, computing device 210 may practically use the collected information to further the treatment plan.

Figure 5:
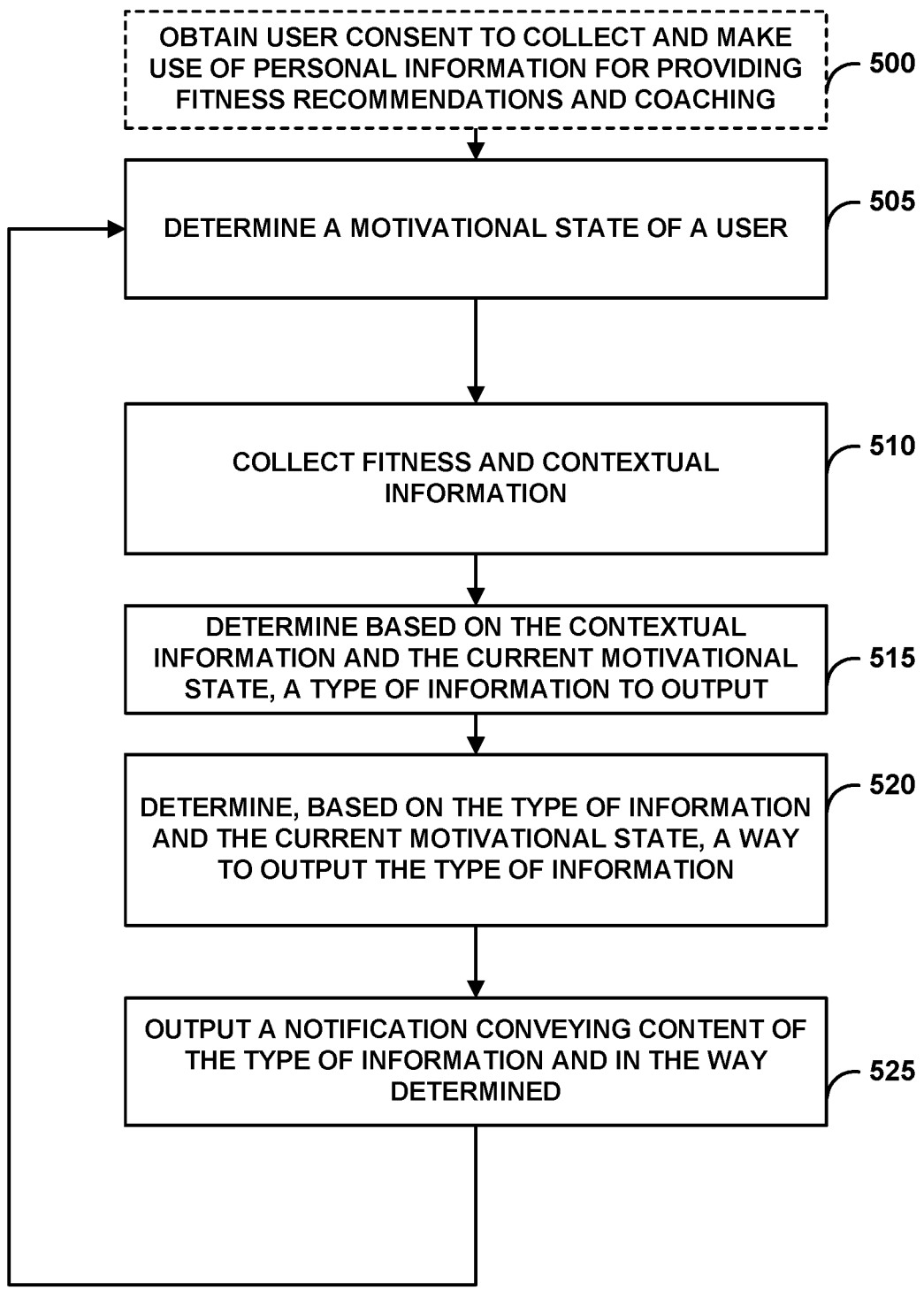
FIG. 5 is a flowchart illustrating example operations of an example computing device configured to provide personalized, and contextually relevant output that alters user behavior for assisting a user in achieving a behavioral goal, in accordance with one or more aspects of the present disclosure.

FIG. 5 is a flowchart illustrating example operations of an example computing device configured to provide personalized, and contextually relevant output that alters user behavior for assisting a user in achieving a behavioral goal, in accordance with one or more aspects of the present disclosure. The process of FIG. 5 may be performed by one or more processors of a computing device, such as computing device 110 of FIG. 1 and/or computing device 210 of FIG. 2. The steps of the process of FIG. 5 may in some examples, be repeated, omitted, and/or performed in any order. For purposes of illustration, FIG. 5 is described below within the context of computing devices 110 and 210 of FIGS. 1 and 2.

In operation, computing device 210 may obtain user consent to collect and make use of personal information for providing fitness recommendations and coaching (500). For example, computing device 210 may display an alert or banner at UIC 212 that requests user consent. Computing device 210 may provide ample opportunities throughout the process of FIG. 5 for a user to withdraw consent, at which time, computing device 210 may cease performing the process of FIG. 5.

In response to obtaining consent, computing device 210 may output a user interface for obtaining a treatment plan or establishing behavioral goals of a user. In other examples, computing device 210 may receive a treatment plan or behavioral goals from application modules 224 or from a remote computing system (e.g., a physician's computer or network). The treatment plan or goals may include various milestones that a user would like to achieve, a stated timeframe for achieving the goals, etc. Fitness module 220 may store the user provided goals as fitness information stored at fitness information data store 280A.

In response to obtaining consent from the user, computing device 210 may determine a motivational state of the user (505). That is, fitness module 220 may rely on state module 222A to infer based on contextual information and fitness information where a user's motivation is at and how far along the user is in achieving a particular behavioral goal. Initially, each user starts in preparation state 302A.

Computing device 210 may collect fitness and contextual information (510). For example, overtime, as contextual information and fitness information is collected (e.g., from sensors 114, activity tracking modules 164, 272, and device context module 162), fitness module 220, through state module 222A, may transition to subsequent motivation states 302.

Computing device 210 may determine, based on the contextual information and the current motivational state, a type of information to output (515). For example, output module 222B may recognize that previously, educational information was output to help a user of computing device 210 progress through preparation state 302A and that in response to detecting ongoing activity (e.g., walking) suggest some inspirational information to output via UIC 212. For instance, output module 222B may cause UIC 212 to output a notification indicating that a user can make progress towards achieving his or her treatment plan or behavioral goal by slowing down or speeding up their walking pace to effect changes in their heartrate.

Computing device 210 may determine based on the type of information and the current motivational state, a channel to output the type of information (520). For example, output module 222B may rely on rules specifying a particular format or form for outputting information for various states. As other examples, the rules may specify a tone of a computer-generated voice output, or a linguistic tone of a text message. That is, the tone of an output may convey a degree of excitement when output during one motivational state and an output may convey a degree of sympathy or compassion when output during a different motivational state. The rules may specify a format, a form, or a type of output form that is specific to a particular motivational state and/or a particular information type. As other examples, a channel may specify a particular type of output, e.g., a voice-based prompt, an audible notification, a visual notification, and/or a haptic notification. As other examples, a channel may specify a particular surface for the output. For example, a notification on a watch may be more suitable when a user is in an action motivational state whereas a notification on a mobile phone or laptop might be better for motivating purposes when output during a preparation motivational state. That is, output module 222B may output information differently for each of the different motivational states so as to encourage and avoid discouraging a user into progressing to a subsequent motivational state.

As discussed above, in some examples, output module 222B may select the channel by selecting a particular surface on which to output the type of information. In some examples, the selected surface may be a surface included in computing device 210. For instance, output module 222B may select display component 202 of computing device 210 to output the notification. In some examples, the selected surface may be a surface included in a computing device other than computing device 210. For instance, output module 222B may select an output component (e.g., display, speaker, or other output component) of another computing device associated with the user (e.g., a smart watch, desktop or laptop computer, tablet, etc.) to output the notification.

Computing device 210 may output a notification conveying content of the type of information and in the way determined previously (525). For example, output module 222B may cause fitness module 220 to send information to UIC 212 that causes UIC 212 to output an alert (e.g., a notification, popup, banner, message, e-mail, etc.) indicating a suggested exercise or dietary selection to make while the user is in a particular motivational state, and in a particular context. For instance, if state module 222A indicates a user is in a maintenance motivational state, output module 222B may cause fitness module 220 to suggest a user eat a salad when contextual information indicates the user visited fast food restaurants for breakfast and lunch so as to maintain their behavioral change. Where the selected surface is included in another computing device, output module 222B may output, to the other computing device, a request for the other computing device to output the notification. Output module 222B may send the request directly to the other computing device (e.g., via a BLUETOOTH link), or may send the request to the other computing device via one or more servers or other intermediaries (e.g., via the Internet).

FIGS. 6A through 6E are conceptual diagrams illustrating aspects of an example machine-learned model according to example implementations of the present disclosure. FIGS. 6A through 6E are described below in the context of modules 162, 164, 120, 220, 222A, 222B, and 272 of FIGS. 1 and 2. For example, in some instances, machine-learned model 600, as referenced below, may be an example of part of any of modules 162, 164, 120, 220, 222A, 222B, and 272.

Figure 6A:
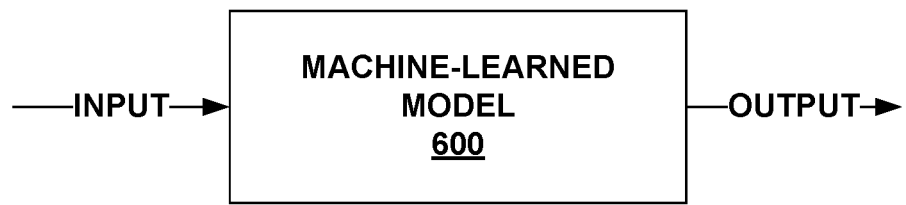
FIGS. 6A through 6E are conceptual diagrams illustrating aspects of an example machine-learned model according to example implementations of the present disclosure.

FIG. 6A depicts a conceptual diagram of an example machine-learned model according to example implementations of the present disclosure. As illustrated in FIG. 6A, in some implementations, machine-learned model 600 is trained to receive input data of one or more types and, in response, provide output data of one or more types. Thus, FIG. 6A illustrates machine-learned model 600 performing inference.

The input data may include one or more features that are associated with an instance or an example. In some implementations, the one or more features associated with the instance or example can be organized into a feature vector. In some implementations, the output data can include one or more predictions. Predictions can also be referred to as inferences. Thus, given features associated with a particular instance, machine-learned model 600 can output a prediction for such instance based on the features.

Machine-learned model 600 can be or include one or more of various different types of machine-learned models. In particular, in some implementations, machine-learned model 600 can perform classification, regression, clustering, anomaly detection, recommendation generation, and/or other tasks.

In some implementations, machine-learned model 600 can perform various types of classification based on the input data. For example, machine-learned model 600 can perform binary classification or multiclass classification. In binary classification, the output data can include a classification of the input data into one of two different classes. In multiclass classification, the output data can include a classification of the input data into one (or more) of more than two classes. The classifications can be single label or multi-label. Machine-learned model 600 may perform discrete categorical classification in which the input data is simply classified into one or more classes or categories.

In some implementations, machine-learned model 600 can perform classification in which machine-learned model 600 provides, for each of one or more classes, a numerical value descriptive of a degree to which it is believed that the input data should be classified into the corresponding class. In some instances, the numerical values provided by machine-learned model 600 can be referred to as "confidence scores" that are indicative of a respective confidence associated with classification of the input into the respective class. In some implementations, the confidence scores can be compared to one or more thresholds to render a discrete categorical prediction. In some implementations, only a certain number of classes (e.g., one) with the relatively largest confidence scores can be selected to render a discrete categorical prediction.

Machine-learned model 600 may output a probabilistic classification. For example, machine-learned model 600 may predict, given a sample input, a probability distribution over a set of classes. Thus, rather than outputting only the most likely class to which the sample input should belong, machine-learned model 600 can output, for each class, a probability that the sample input belongs to such class. In some implementations, the probability distribution over all possible classes can sum to one. In some implementations, a Softmax function, or other type of function or layer can be used to squash a set of real values respectively associated with the possible classes to a set of real values in the range (0, 1) that sum to one.

In some examples, the probabilities provided by the probability distribution can be compared to one or more thresholds to render a discrete categorical prediction. In some implementations, only a certain number of classes (e.g., one) with the relatively largest predicted probability can be selected to render a discrete categorical prediction.

In cases in which machine-learned model 600 performs classification, machine-learned model 600 may be trained using supervised learning techniques. For example, machine-learned model 600 may be trained on a training dataset that includes training examples labeled as belonging (or not belonging) to one or more classes. Further details regarding supervised training techniques are provided below in the descriptions of FIGS. 6B through 6E.

In some implementations, machine-learned model 600 can perform regression to provide output data in the form of a continuous numeric value. The continuous numeric value can correspond to any number of different metrics or numeric representations, including, for example, currency values, scores, or other numeric representations. As examples, machine-learned model 600 can perform linear regression, polynomial regression, or nonlinear regression. As examples, machine-learned model 600 can perform simple regression or multiple regression. As described above, in some implementations, a Softmax function or other function or layer can be used to squash a set of real values respectively associated with a two or more possible classes to a set of real values in the range (0, 1) that sum to one.

Machine-learned model 600 may perform various types of clustering. For example, machine-learned model 600 can identify one or more previously-defined clusters to which the input data most likely corresponds. Machine-learned model 600 may identify one or more clusters within the input data. That is, in instances in which the input data includes multiple objects, documents, or other entities, machine-learned model 600 can sort the multiple entities included in the input data into a number of clusters. In some implementations in which machine-learned model 600 performs clustering, machine-learned model 600 can be trained using unsupervised learning techniques.

Machine-learned model 600 may perform anomaly detection or outlier detection. For example, machine-learned model 600 can identify input data that does not conform to an expected pattern or other characteristic (e.g., as previously observed from previous input data). As examples, the anomaly detection can be used for fraud detection or system failure detection.

In some implementations, machine-learned model 600 can provide output data in the form of one or more recommendations. For example, machine-learned model 600 can be included in a recommendation system or engine. As an example, given input data that describes previous outcomes for certain entities (e.g., a score, ranking, or rating indicative of an amount of success or enjoyment), machine-learned model 600 can output a suggestion or recommendation of one or more additional entities that, based on the previous outcomes, are expected to have a desired outcome (e.g., elicit a score, ranking, or rating indicative of success or enjoyment). As one example, given input data descriptive of a context of a computing device, such as computing device 110 of FIG. 1, a suggestion system, such as fitness module 220 of FIG. 2, can output a suggestion or recommendation of behavioral changes the user may make to progress towards achieving a behavioral goal.

Machine-learned model 600 may, in some cases, act as an agent within an environment. For example, machine-learned model 600 can be trained using reinforcement learning, which will be discussed in further detail below.

In some implementations, machine-learned model 600 can be a parametric model while, in other implementations, machine-learned model 600 can be a non-parametric model. In some implementations, machine-learned model 600 can be a linear model while, in other implementations, machine-learned model 600 can be a non-linear model.

As described above, machine-learned model 600 can be or include one or more of various different types of machine-learned models. Examples of such different types of machine-learned models are provided below for illustration. One or more of the example models described below can be used (e.g., combined) to provide the output data in response to the input data. Additional models beyond the example models provided below can be used as well.

In some implementations, machine-learned model 600 can be or include one or more classifier models such as, for example, linear classification models; quadratic classification models; etc. Machine-learned model 600 may be or include one or more regression models such as, for example, simple linear regression models; multiple linear regression models; logistic regression models; stepwise regression models; multivariate adaptive regression splines; locally estimated scatterplot smoothing models; etc.

In some examples, machine-learned model 600 can be or include one or more decision tree-based models such as, for example, classification and/or regression trees; iterative dichotomiser 3 decision trees; C4.5 decision trees; chi-squared automatic interaction detection decision trees; decision stumps; conditional decision trees; etc.

Machine-learned model 600 may be or include one or more kernel machines. In some implementations, machine-learned model 600 can be or include one or more support vector machines. Machine-learned model 600 may be or include one or more instance-based learning models such as, for example, learning vector quantization models; self-organizing map models; locally weighted learning models; etc. In some implementations, machine-learned model 600 can be or include one or more nearest neighbor models such as, for example, k-nearest neighbor classifications models; k-nearest neighbors regression models; etc. Machine-learned model 600 can be or include one or more Bayesian models such as, for example, naïve Bayes models; Gaussian naïve Bayes models; multinomial naïve Bayes models; averaged one-dependence estimators; Bayesian networks; Bayesian belief networks; hidden Markov models; etc.

In some implementations, machine-learned model 600 can be or include one or more artificial neural networks (also referred to simply as neural networks). A neural network can include a group of connected nodes, which also can be referred to as neurons or perceptrons. A neural network can be organized into one or more layers. Neural networks that include multiple layers can be referred to as "deep" networks. A deep network can include an input layer, an output layer, and one or more hidden layers positioned between the input layer and the output layer. The nodes of the neural network can be connected or non-fully connected.

Machine-learned model 600 can be or include one or more feed forward neural networks. In feed forward networks, the connections between nodes do not form a cycle. For example, each connection can connect a node from an earlier layer to a node from a later layer.

In some instances, machine-learned model 600 can be or include one or more recurrent neural networks. In some instances, at least some of the nodes of a recurrent neural network can form a cycle. Recurrent neural networks can be especially useful for processing input data that is sequential in nature. In particular, in some instances, a recurrent neural network can pass or retain information from a previous portion of the input data sequence to a subsequent portion of the input data sequence through the use of recurrent or directed cyclical node connections.

In some examples, sequential input data can include time-series data (e.g., sensor data versus time or imagery captured at different times). For example, a recurrent neural network can analyze sensor data versus time to detect or predict a swipe direction, to perform handwriting recognition, etc. Sequential input data may include words in a sentence (e.g., for natural language processing, speech detection or processing, etc.); notes in a musical composition; sequential actions taken by a user (e.g., to detect or predict sequential application usage); sequential object states; etc.

Example recurrent neural networks include long short-term (LSTM) recurrent neural networks; gated recurrent units; bi-direction recurrent neural networks; continuous time recurrent neural networks; neural history compressors; echo state networks; Elman networks; Jordan networks; recursive neural networks; Hopfield networks; fully recurrent networks; sequence-to-sequence configurations; etc.

In some implementations, machine-learned model 600 can be or include one or more convolutional neural networks. In some instances, a convolutional neural network can include one or more convolutional layers that perform convolutions over input data using learned filters.

Filters can also be referred to as kernels. Convolutional neural networks can be especially useful for vision problems such as when the input data includes imagery such as still images or video. However, convolutional neural networks can also be applied for natural language processing.

In some examples, machine-learned model 600 can be or include one or more generative networks such as, for example, generative adversarial networks. Generative networks can be used to generate new data such as new images or other content.

Machine-learned model 600 may be or include an autoencoder. In some instances, the aim of an autoencoder is to learn a representation (e.g., a lower-dimensional encoding) for a set of data, typically for the purpose of dimensionality reduction. For example, in some instances, an autoencoder can seek to encode the input data and the provide output data that reconstructs the input data from the encoding. Recently, the autoencoder concept has become more widely used for learning generative models of data. In some instances, the autoencoder can include additional losses beyond reconstructing the input data.

Machine-learned model 600 may be or include one or more other forms of artificial neural networks such as, for example, deep Boltzmann machines; deep belief networks; stacked autoencoders; etc. Any of the neural networks described herein can be combined (e.g., stacked) to form more complex networks.

One or more neural networks can be used to provide an embedding based on the input data. For example, the embedding can be a representation of knowledge abstracted from the input data into one or more learned dimensions. In some instances, embeddings can be a useful source for identifying related entities. In some instances, embeddings can be extracted from the output of the network, while in other instances embeddings can be extracted from any hidden node or layer of the network (e.g., a close to final but not final layer of the network). Embeddings can be useful for performing auto suggest next video, product suggestion, entity or object recognition, etc. In some instances, embeddings be useful inputs for downstream models. For example, embeddings can be useful to generalize input data (e.g., search queries) for a downstream model or processing system.

Machine-learned model 600 may include one or more clustering models such as, for example, k-means clustering models; k-medians clustering models; expectation maximization models; hierarchical clustering models; etc.

In some implementations, machine-learned model 600 can perform one or more dimensionality reduction techniques such as, for example, principal component analysis; kernel principal component analysis; graph-based kernel principal component analysis; principal component regression; partial least squares regression; Sammon mapping; multidimensional scaling; projection pursuit; linear discriminant analysis; mixture discriminant analysis; quadratic discriminant analysis; generalized discriminant analysis; flexible discriminant analysis; autoencoding; etc.

In some implementations, machine-learned model 600 can perform or be subjected to one or more reinforcement learning techniques such as Markov decision processes; dynamic programming; Q functions or Q-learning; value function approaches; deep Q-networks; differentiable neural computers; asynchronous advantage actor-critics; deterministic policy gradient; etc.

In some implementations, machine-learned model 600 can be an autoregressive model. In some instances, an autoregressive model can specify that the output data depends linearly on its own previous values and on a stochastic term. In some instances, an autoregressive model can take the form of a stochastic difference equation. One example autoregressive model is WaveNet, which is a generative model for raw audio.

In some implementations, machine-learned model 600 can include or form part of a multiple model ensemble. As one example, bootstrap aggregating can be performed, which can also be referred to as "bagging." In bootstrap aggregating, a training dataset is split into a number of subsets (e.g., through random sampling with replacement) and a plurality of models are respectively trained on the number of subsets. At inference time, respective outputs of the plurality of models can be combined (e.g., through averaging, voting, or other techniques) and used as the output of the ensemble.

One example ensemble is a random forest, which can also be referred to as a random decision forest. Random forests are an ensemble learning method for classification, regression, and other tasks. Random forests are generated by producing a plurality of decision trees at training time. In some instances, at inference time, the class that is the mode of the classes (classification) or the mean prediction (regression) of the individual trees can be used as the output of the forest. Random decision forests can correct for decision trees' tendency to overfit their training set.

Another example ensemble technique is stacking, which can, in some instances, be referred to as stacked generalization. Stacking includes training a combiner model to blend or otherwise combine the predictions of several other machine-learned models. Thus, a plurality of machine-learned models (e.g., of same or different type) can be trained based on training data. In addition, a combiner model can be trained to take the predictions from the other machine-learned models as inputs and, in response, produce a final inference or prediction. In some instances, a single-layer logistic regression model can be used as the combiner model.

Another example ensemble technique is boosting. Boosting can include incrementally building an ensemble by iteratively training weak models and then adding to a final strong model. For example, in some instances, each new model can be trained to emphasize the training examples that previous models misinterpreted (e.g., misclassified). For example, a weight associated with each of such misinterpreted examples can be increased. One common implementation of boosting is AdaBoost, which can also be referred to as Adaptive Boosting. Other example boosting techniques include LPBoost; TotalBoost; BrownBoost; xgboost; MadaBoost, LogitBoost, gradient boosting; etc. Furthermore, any of the models described above (e.g., regression models and artificial neural networks) can be combined to form an ensemble. As an example, an ensemble can include a top-level machine-learned model or a heuristic function to combine and/or weight the outputs of the models that form the ensemble.

In some implementations, multiple machine-learned models (e.g., that form an ensemble can be linked and trained jointly (e.g., through backpropagation of errors sequentially through the model ensemble). However, in some implementations, only a subset (e.g., one) of the jointly trained models is used for inference.

In some implementations, machine-learned model 600 can be used to preprocess the input data for subsequent input into another model. For example, machine-learned model 600 can perform dimensionality reduction techniques and embeddings (e.g., matrix factorization, principal components analysis, singular value decomposition, word2vec/GLOVE, and/or related approaches); clustering; and even classification and regression for downstream consumption. Many of these techniques have been discussed above and will be further discussed below.

As discussed above, machine-learned model 600 can be trained or otherwise configured to receive the input data and, in response, provide the output data. The input data can include different types, forms, or variations of input data. As examples, in various implementations, the input data can include features that describe the content (or portion of content) initially selected by the user, e.g., content of user-selected document or image, links pointing to the user selection, links within the user selection relating to other files available on device or cloud, metadata of user selection, etc. Additionally, with user permission, the input data includes the context of user usage, either obtained from app itself or from other sources. Examples of usage context include breadth of share (sharing publicly, or with a large group, or privately, or a specific person), context of share, etc. When permitted by the user, additional input data can include the state of the device, e.g., the location of the device, the apps running on the device, etc.

In some implementations, machine-learned model 600 can receive and use the input data in its raw form. In some implementations, the raw input data can be preprocessed. Thus, in addition or alternatively to the raw input data, machine-learned model 600 can receive and use the preprocessed input data.

In some implementations, preprocessing the input data can include extracting one or more additional features from the raw input data. For example, feature extraction techniques can be applied to the input data to generate one or more new, additional features. Example feature extraction techniques include edge detection; corner detection; blob detection; ridge detection; scale-invariant feature transform; motion detection; optical flow; Hough transform; etc.

In some implementations, the extracted features can include or be derived from transformations of the input data into other domains and/or dimensions. As an example, the extracted features can include or be derived from transformations of the input data into the frequency domain. For example, wavelet transformations and/or fast Fourier transforms can be performed on the input data to generate additional features.

In some implementations, the extracted features can include statistics calculated from the input data or certain portions or dimensions of the input data. Example statistics include the mode, mean, maximum, minimum, or other metrics of the input data or portions thereof.

In some implementations, as described above, the input data can be sequential in nature. In some instances, the sequential input data can be generated by sampling or otherwise segmenting a stream of input data. As one example, frames can be extracted from a video. In some implementations, sequential data can be made non-sequential through summarization.

As another example preprocessing technique, portions of the input data can be imputed. For example, additional synthetic input data can be generated through interpolation and/or extrapolation.

As another example preprocessing technique, some or all of the input data can be scaled, standardized, normalized, generalized, and/or regularized. Example regularization techniques include ridge regression; least absolute shrinkage and selection operator (LASSO); elastic net; least-angle regression; cross-validation; L1 regularization; L2 regularization; etc. As one example, some or all of the input data can be normalized by subtracting the mean across a given dimension's feature values from each individual feature value and then dividing by the standard deviation or other metric.

As another example preprocessing technique, some or all or the input data can be quantized or discretized. In some cases, qualitative features or variables included in the input data can be converted to quantitative features or variables. For example, one hot encoding can be performed.

In some examples, dimensionality reduction techniques can be applied to the input data prior to input into machine-learned model 600. Several examples of dimensionality reduction techniques are provided above, including, for example, principal component analysis; kernel principal component analysis; graph-based kernel principal component analysis; principal component regression; partial least squares regression; Sammon mapping; multidimensional scaling; projection pursuit; linear discriminant analysis; mixture discriminant analysis; quadratic discriminant analysis; generalized discriminant analysis; flexible discriminant analysis; autoencoding; etc.

In some implementations, during training, the input data can be intentionally deformed in any number of ways to increase model robustness, generalization, or other qualities. Example techniques to deform the input data include adding noise; changing color, shade, or hue; magnification; segmentation; amplification; etc.

In response to receipt of the input data, machine-learned model 600 can provide the output data. The output data can include different types, forms, or variations of output data. As examples, in various implementations, the output data can include content, either stored locally on the user device or in the cloud, that is relevantly shareable along with the initial content selection.

As discussed above, in some implementations, the output data can include various types of classification data (e.g., binary classification, multiclass classification, single label, multi-label, discrete classification, regressive classification, probabilistic classification, etc.) or can include various types of regressive data (e.g., linear regression, polynomial regression, nonlinear regression, simple regression, multiple regression, etc.). In other instances, the output data can include clustering data, anomaly detection data, recommendation data, or any of the other forms of output data discussed above.

In some implementations, the output data can influence downstream processes or decision making. As one example, in some implementations, the output data can be interpreted and/or acted upon by a rules-based regulator.

The present disclosure provides systems and methods that include or otherwise leverage one or more machine-learned models to suggest content, either stored locally on the uses device or in the cloud, that is relevantly shareable along with the initial content selection based on features of the initial content selection. Any of the different types or forms of input data described above can be combined with any of the different types or forms of machine-learned models described above to provide any of the different types or forms of output data described above.

The systems and methods of the present disclosure can be implemented by or otherwise executed on one or more computing devices. Example computing devices include user computing devices (e.g., laptops, desktops, and mobile computing devices such as tablets, smartphones, wearable computing devices, etc.); embedded computing devices (e.g., devices embedded within a vehicle, camera, image sensor, industrial machine, satellite, gaming console or controller, or home appliance such as a refrigerator, thermostat, energy meter, home energy manager, smart home assistant, etc.); server computing devices (e.g., database servers, parameter servers, file servers, mail servers, print servers, web servers, game servers, application servers, etc.); dedicated, specialized model processing or training devices; virtual computing devices; other computing devices or computing infrastructure; or combinations thereof.

Figure 6B:
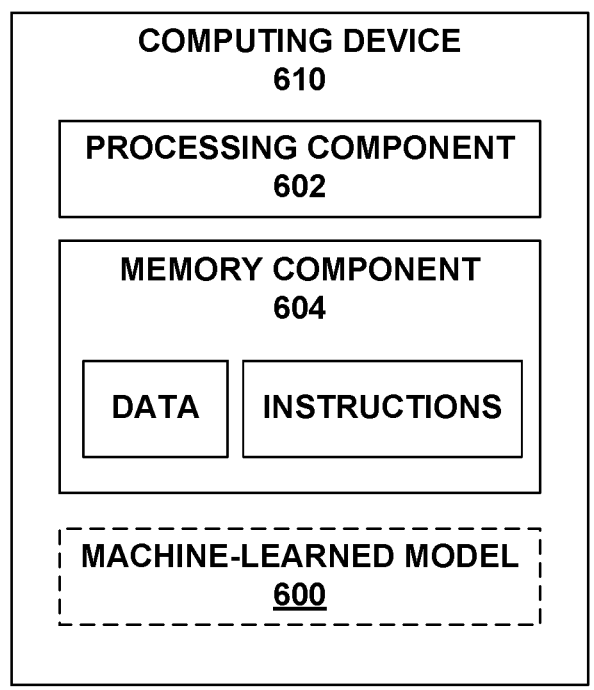

FIG. 6B illustrates a conceptual diagram of computing device 610, which is an example of computing device 110 of FIG. 1. Computing device 610 includes processing component 602, memory component 604 and machine-learned model 600. Computing device 610 may store and implement machine-learned model 600 locally (i.e., on-device). Thus, in some implementations, machine-learned model 600 can be stored at and/or implemented locally by an embedded device or a user computing device such as a mobile device. Output data obtained through local implementation of machine-learned model 600 at the embedded device or the user computing device can be used to improve performance of the embedded device or the user computing device (e.g., an application implemented by the embedded device or the user computing device).

Figure 6C:
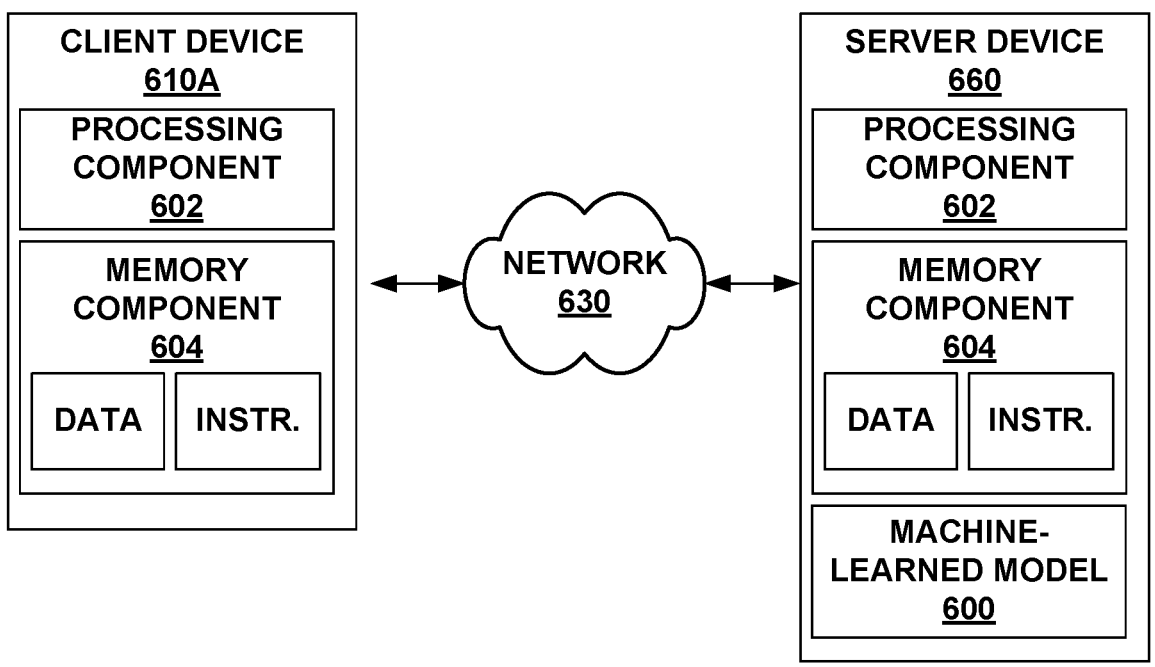

FIG. 6C illustrates a conceptual diagram of an example client computing device that can communicate over a network with an example server computing system that includes a machine-learned model. FIG. 6C includes client device 610A communicating with server device 660 over network 630. Client device 610A is an example of computing device 110 of FIG. 1, server device 660 is an example of computing system 160 of FIG. 1 6, and network 630 is an example of network 130 of FIG. 1. Server device 660 stores and implements machine-learned model 600. In some instances, output data obtained through machine-learned model 600 at server device 660 can be used to improve other server tasks or can be used by other non-user devices to improve services performed by or for such other non-user devices. For example, the output data can improve other downstream processes performed by server device 660 for a computing device of a user or embedded computing device. In other instances, output data obtained through implementation of machine-learned model 600 at server device 660 can be sent to and used by a user computing device, an embedded computing device, or some other client device, such as client device 610A. For example, server device 660 can be said to perform machine learning as a service.

In yet other implementations, different respective portions of machine-learned model 600 can be stored at and/or implemented by some combination of a user computing device; an embedded computing device; a server computing device; etc. In other words, portions of machine-learned model 600 may be distributed in whole or in part amongst client device 610A and server device 660.

Devices 610A and 660 may perform graph processing techniques or other machine learning techniques using one or more machine learning platforms, frameworks, and/or libraries, such as, for example, TensorFlow, Caffe/Caffe2, Theano, Torch/PyTorch, MXnet, CNTK, etc. Devices 610A and 660 may be distributed at different physical locations and connected via one or more networks, including network 330. If configured as distributed computing devices, Devices 610A and 660 may operate according to sequential computing architectures, parallel computing architectures, or combinations thereof. In one example, distributed computing devices can be controlled or guided through use of a parameter server.

In some implementations, multiple instances of machine-learned model 600 can be parallelized to provide increased processing throughput. For example, the multiple instances of machine-learned model 600 can be parallelized on a single processing device or computing device or parallelized across multiple processing devices or computing devices.

Each computing device that implements machine-learned model 600 or other aspects of the present disclosure can include a number of hardware components that enable performance of the techniques described herein. For example, each computing device can include one or more memory devices that store some or all of machine-learned model 600. For example, machine-learned model 600 can be a structured numerical representation that is stored in memory. The one or more memory devices can also include instructions for implementing machine-learned model 600 or performing other operations. Example memory devices include RAM, ROM, EEPROM, EPROM, flash memory devices, magnetic disks, etc., and combinations thereof.

Each computing device can also include one or more processing devices that implement some or all of machine-learned model 600 and/or perform other related operations. Example processing devices include one or more of: a central processing unit (CPU); a visual processing unit (VPU); a graphics processing unit (GPU); a tensor processing unit (TPU); a neural processing unit (NPU); a neural processing engine; a core of a CPU, VPU, GPU, TPU, NPU or other processing device; an application specific integrated circuit (ASIC); a field programmable gate array (FPGA); a co-processor; a controller; or combinations of the processing devices described above. Processing devices can be embedded within other hardware components such as, for example, an image sensor, accelerometer, etc.

Hardware components (e.g., memory devices and/or processing devices) can be spread across multiple physically distributed computing devices and/or virtually distributed computing systems.

Figure 6D:
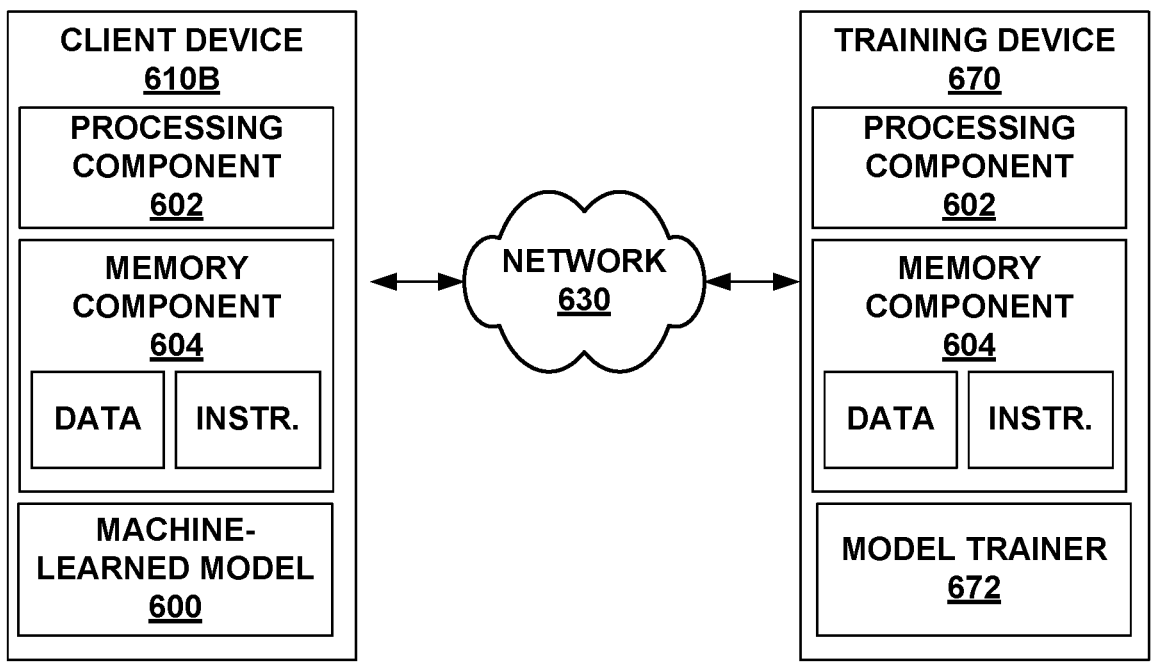

FIG. 6D illustrates a conceptual diagram of an example computing device in communication with an example training computing system that includes a model trainer. FIG. 6D includes client device 610B communicating with training device 670 over network 630. Client device 610B is an example of computing device 110 of FIG. 1 and network 630 is an example of network 130 of FIG. 1. Machine-learned model 600 described herein can be trained at a training computing system, such as training device 670, and then provided for storage and/or implementation at one or more computing devices, such as client device 610B. For example, model trainer 672 executes locally at training device 670. However in some examples, training device 670, including model trainer 672, can be included in or separate from client device 610B or any other computing device that implement machine-learned model 600.

In some implementations, machine-learned model 600 may be trained in an offline fashion or an online fashion. In offline training (also known as batch learning), machine-learned model 600 is trained on the entirety of a static set of training data. In online learning, machine-learned model 600 is continuously trained (or re-trained) as new training data becomes available (e.g., while the model is used to perform inference).

Model trainer 672 may perform centralized training of machine-learned model 600 (e.g., based on a centrally stored dataset). In other implementations, decentralized training techniques such as distributed training, federated learning, or the like can be used to train, update, or personalize machine-learned model 600.

Machine-learned model 600 described herein can be trained according to one or more of various different training types or techniques. For example, in some implementations, machine-learned model 600 can be trained by model trainer 672 using supervised learning, in which machine-learned model 600 is trained on a training dataset that includes instances or examples that have labels. The labels can be manually applied by experts, generated through crowd-sourcing, or provided by other techniques (e.g., by physics-based or complex mathematical models). In some implementations, if the user has provided consent, the training examples can be provided by the user computing device. In some implementations, this process can be referred to as personalizing the model.

Figure 6E:
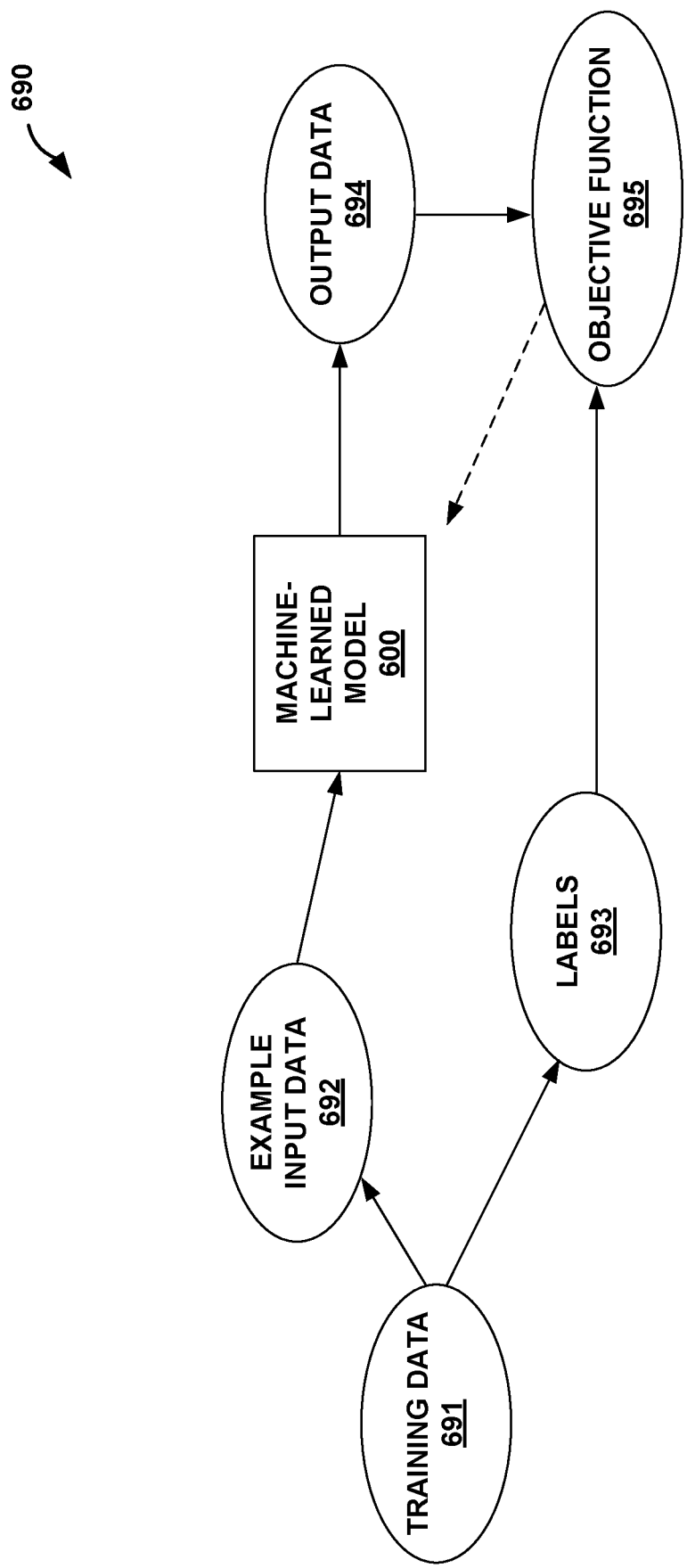

FIG. 6E illustrates a conceptual diagram of training process 690 which is an example training process in which machine-learned model 600 is trained on training data 391 that includes example input data 692 that has labels 693. Training processes 690 is one example training process; other training processes may be used as well.

Training data 691 used by training process 690 can include, upon user permission for use of such data for training, anonymized usage logs of sharing flows, e.g., content items that were shared together, bundled content pieces already identified as belonging together, e.g., from entities in a knowledge graph, etc. In some implementations, training data 691 can include examples of input data 692 that have been assigned labels 693 that correspond to output data 694.

In some implementations, machine-learned model 600 can be trained by optimizing an objective function, such as objective function 695. For example, in some implementations, objective function 695 may be or include a loss function that compares (e.g., determines a difference between) output data generated by the model from the training data and labels (e.g., ground-truth labels) associated with the training data. For example, the loss function can evaluate a sum or mean of squared differences between the output data and the labels. In some examples, objective function 695 may be or include a cost function that describes a cost of a certain outcome or output data. Other examples of objective function 695 can include margin-based techniques such as, for example, triplet loss or maximum-margin training.

One or more of various optimization techniques can be performed to optimize objective function 695. For example, the optimization technique(s) can minimize or maximize objective function 695. Example optimization techniques include Hessian-based techniques and gradient-based techniques, such as, for example, coordinate descent; gradient descent (e.g., stochastic gradient descent); subgradient methods; etc. Other optimization techniques include black box optimization techniques and heuristics.

In some implementations, backward propagation of errors can be used in conjunction with an optimization technique (e.g., gradient based techniques) to train machine-learned model 600 (e.g., when machine-learned model is a multi-layer model such as an artificial neural network). For example, an iterative cycle of propagation and model parameter (e.g., weights) update can be performed to train machine-learned model 600. Example backpropagation techniques include truncated backpropagation through time, Levenberg-Marquardt backpropagation, etc.

In some implementations, machine-learned model 600 described herein can be trained using unsupervised learning techniques. Unsupervised learning can include inferring a function to describe hidden structure from unlabeled data. For example, a classification or categorization may not be included in the data. Unsupervised learning techniques can be used to produce machine-learned models capable of performing clustering, anomaly detection, learning latent variable models, or other tasks.

Machine-learned model 600 can be trained using semi-supervised techniques which combine aspects of supervised learning and unsupervised learning. Machine-learned model 600 can be trained or otherwise generated through evolutionary techniques or genetic algorithms. In some implementations, machine-learned model 600 described herein can be trained using reinforcement learning. In reinforcement learning, an agent (e.g., model) can take actions in an environment and learn to maximize rewards and/or minimize penalties that result from such actions. Reinforcement learning can differ from the supervised learning problem in that correct input/output pairs are not presented, nor sub-optimal actions explicitly corrected.

In some implementations, one or more generalization techniques can be performed during training to improve the generalization of machine-learned model 600. Generalization techniques can help reduce overfitting of machine-learned model 600 to the training data. Example generalization techniques include dropout techniques; weight decay techniques; batch normalization; early stopping; subset selection; stepwise selection; etc.

In some implementations, machine-learned model 600 described herein can include or otherwise be impacted by a number of hyperparameters, such as, for example, learning rate, number of layers, number of nodes in each layer, number of leaves in a tree, number of clusters; etc. Hyperparameters can affect model performance. Hyperparameters can be hand selected or can be automatically selected through application of techniques such as, for example, grid search; black box optimization techniques (e.g., Bayesian optimization, random search, etc.); gradient-based optimization; etc. Example techniques and/or tools for performing automatic hyperparameter optimization include Hyperopt; Auto-WEKA; Spearmint; Metric Optimization Engine (MOE); etc.

In some implementations, various techniques can be used to optimize and/or adapt the learning rate when the model is trained. Example techniques and/or tools for performing learning rate optimization or adaptation include Adagrad; Adaptive Moment Estimation (ADAM); Adadelta; RMSprop; etc.

In some implementations, transfer learning techniques can be used to provide an initial model from which to begin training of machine-learned model 600 described herein.

In some implementations, machine-learned model 600 described herein can be included in different portions of computer-readable code on a computing device. In one example, machine-learned model 600 can be included in a particular application or program and used (e.g., exclusively) by such particular application or program. Thus, in one example, a computing device can include a number of applications and one or more of such applications can contain its own respective machine learning library and machine-learned model(s).

In another example, machine-learned model 600 described herein can be included in an operating system of a computing device (e.g., in a central intelligence layer of an operating system) and can be called or otherwise used by one or more applications that interact with the operating system. In some implementations, each application can communicate with the central intelligence layer (and model(s) stored therein) using an application programming interface (API) (e.g., a common, public API across all applications).

In some implementations, the central intelligence layer can communicate with a central device data layer. The central device data layer can be a centralized repository of data for the computing device. The central device data layer can communicate with a number of other components of the computing device, such as, for example, one or more sensors, a context manager, a device state component, and/or additional components. In some implementations, the central device data layer can communicate with each device component using an API (e.g., a private API).

The technology discussed herein makes reference to servers, databases, software applications, and other computer-based systems, as well as actions taken and information sent to and from such systems. The inherent flexibility of computer-based systems allows for a great variety of possible configurations, combinations, and divisions of tasks and functionality between and among components. For instance, processes discussed herein can be implemented using a single device or component or multiple devices or components working in combination.

Databases and applications can be implemented on a single system or distributed across multiple systems. Distributed components can operate sequentially or in parallel.

In addition, the machine learning techniques described herein are readily interchangeable and combinable. Although certain example techniques have been described, many others exist and can be used in conjunction with aspects of the present disclosure.

A brief overview of example machine-learned models and associated techniques has been provided by the present disclosure. For additional details, readers should review the following references: Machine Learning A Probabilistic Perspective (Murphy); Rules of Machine Learning: Best Practices for ML Engineering (Zinkevich); Deep Learning (Goodfellow); Reinforcement Learning: An Introduction (Sutton); and Artificial Intelligence: A Modern Approach (Norvig).

Further to the descriptions above, a user may be provided with controls allowing the user to make an election as to both if and when systems, programs or features described herein may enable collection of user information (e.g., information about a user's social network, social actions or activities, profession, a user's preferences, or a user's current location), and if the user is sent content or communications from a server. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over what information is collected about the user, how that information is used, and what information is provided to the user.

Clause 1. A method, comprising: obtaining, by a computing device, user consent to collect and make use of personal information for providing behavioral coaching; obtaining, by the computing device, contextual and fitness related information of a user; determining, by the computing device, by inputting the contextual and fitness related information into a model that defines a motivational state, a current motivational state of the user; determining, based at least in part on the current motivational state of the user, a type of information to output as part of the behavioral coaching, wherein the type of information is selected from a group comprising education information, inspirational information, and achievement information; determining, based on the type of information to output, a channel for outputting the type of information as part of the behavioral coaching; and outputting, by the computing device, via the channel, a notification including content of the type of information.

Clause 2. The method of clause 1, wherein the current motivational state of the user is determined from a plurality of motivational states, and wherein the plurality of motivational states includes one or more of a preparation state, an action state, a maintenance state, and a regress state.

Clause 3. The method of clause 1 or 2, wherein determining the current motivational state of the user comprises determining a first motivational state of the user at a first time, the method further comprising: obtaining, by the computing device and after the first time, second contextual and fitness related information of the user; determining, by the computing device, by inputting the second contextual and fitness related information into the model, a second motivational state of the user.

Clause 4. The method of clause 3, wherein determining the second motivational state of the user comprises: obtaining transition rules between the first motivational state and the second motivational state, wherein determining the second motivational state of the user comprises determining, based on the transition rules and the second contextual and fitness related information, that the user has transitioned to the second motivational state.

Clause 5. The method of clause 4, wherein determining the type of information to output comprises: responsive to determining that the user has transitioned to the second motivational state, determining an initial type of information to output.

Clause 6. The method of any combination of clauses 1-5, wherein determining the channel for outputting the type of information comprises: selecting, based on one or more rules, a particular format or form for outputting the notification including content of the type of information.

Clause 7. The method of clause 6, wherein selecting the particular format or form comprises: selecting a particular surface on which to output the notification including content of the type of information.

Clause 8. The method of clause 7, wherein: the computing device is a first computing device, selecting the particular surface comprises selecting a display of a second computing device, the second computing device being different than the first computing device, and outputting the notification via the channel comprises outputting, by the first computing device, a request for the second computing device to output the notification.

Clause 9. The method of clause 8, wherein the second computing device is a wearable computing device.

Clause 10. The method of clause 9, wherein selecting the display of the second computing device comprises selecting the display of the second computing device responsive to determining that the current motivational state of the user is an action motivational state.

Clause 11. A system comprising means for performing the method of any combinations of clauses 1-11.

Clause 12. A computing device comprising means for performing the method of any combinations of clauses 1-11.

Clause 13. A computing device comprising at least one processor configured to perform the method of any combinations of clauses 1-11.

In one or more examples, the functions described may be implemented in hardware, software, firmware, or any combination thereof. If implemented in software, the functions may be stored on or transmitted over, as one or more instructions or code, a computer-readable medium and executed by a hardware-based processing unit. Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) tangible computer-readable storage media, which is non-transitory or (2) a communication medium such as a signal or carrier wave. Data storage media may be any available media that can be accessed by one or more computers or one or more processors to retrieve instructions, code and/or data structures for implementation of the techniques described in this disclosure. A computer program product may include a computer-readable medium.

By way of example, and not limitation, such computer-readable storage media can comprise RAM, ROM, EEPROM, CD-ROM or other optical disk storage, magnetic disk storage, or other magnetic storage devices, flash memory, or any other medium that can be used to store desired program code in the form of instructions or data structures and that can be accessed by a computer. Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transient media, but are instead directed to non-transient, tangible storage media. Disk and disc, as used herein, includes compact disc (CD), laser disc, optical disc, digital versatile disc (DVD), floppy disk and Blu-ray disc, where disks usually reproduce data magnetically, while discs reproduce data optically with lasers. Combinations of the above should also be included within the scope of computer-readable media.

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor," as used herein may refer to any of the foregoing structure or any other structure suitable for implementation of the techniques described herein. In addition, in some aspects, the functionality described herein may be provided within dedicated hardware and/or software modules. Also, the techniques could be fully implemented in one or more circuits or logic elements.

The techniques of this disclosure may be implemented in a wide variety of devices or apparatuses, including a wireless handset, an integrated circuit (IC) or a set of ICs (e.g., a chip set). Various components, modules, or units are described in this disclosure to emphasize functional aspects of devices configured to perform the disclosed techniques, but do not necessarily require realization by different hardware units. Rather, as described above, various units may be combined in a hardware unit or provided by a collection of interoperable hardware units, including one or more processors as described above, in conjunction with suitable software and/or firmware.

Various examples have been described. These and other examples are within the scope of the following claims.

What is claimed is:

1. A method, comprising:
obtaining, by a first computing device, user consent to collect and make use of personal information for providing behavioral coaching;
obtaining, by the first computing device, contextual and fitness related information of a user;
determining, by the first computing device, by inputting the contextual and fitness related information into a model that defines a motivational state, a current motivational state of the user;
determining, based at least in part on the current motivational state of the user, a type of information to output as part of the behavioral coaching, wherein the type of information is selected from a group comprising education information, inspirational information, and achievement information;
determining, based on the type of information to output, a channel for outputting the type of information as part of the behavioral coaching; and
outputting, by the first computing device, via the channel, a notification including content of the type of information, wherein:
determining the channel for outputting the type of information comprises selecting, based on one or more rules, a particular surface on which to output the notification including content of the type of information,
selecting the particular surface comprises selecting a display of a second computing device, the second computing device being different than the first computing device, and
outputting the notification via the channel comprises outputting, by the first computing device, a request for the second computing device to output the notification.

2. The method of claim 1, wherein the current motivational state of the user is determined from a plurality of motivational states, and wherein the plurality of motivational states includes one or more of a preparation state, an action state, a maintenance state, and a regress state.

3. The method of claim 1, wherein determining the current motivational state of the user comprises determining a first motivational state of the user at a first time, the method further comprising:
obtaining, by the first computing device and after the first time, second contextual and fitness related information of the user; and
determining, by the first computing device, by inputting the second contextual and fitness related information into the model, a second motivational state of the user.

4. The method of claim 3, wherein determining the second motivational state of the user comprises:
obtaining transition rules between the first motivational state and the second motivational state,
wherein determining the second motivational state of the user comprises determining, based on the transition rules and the second contextual and fitness related information, that the user has transitioned to the second motivational state.

5. The method of claim 4, wherein determining the type of information to output comprises:
responsive to determining that the user has transitioned to the second motivational state, determining an initial type of information to output.

6. The method of claim 1, wherein the second computing device is a wearable computing device.

7. The method of claim 6, wherein selecting the display of the second computing device comprises selecting the display of the second computing device responsive to determining that the current motivational state of the user is an action motivational state.

8. A first computing device comprising:
at least one processor;
memory comprising instructions that, when executed by the at least one processor, cause the at least one processor to:
obtain user consent to collect and make use of personal information for providing behavioral coaching;
obtain contextual and fitness related information of a user;
determine, by inputting the contextual and fitness related information into a model that defines a motivational state, a current motivational state of the user;
determine, based at least in part on the current motivational state of the user, a type of information to output as part of the behavioral coaching, wherein the type of information is selected from a group comprising education information, inspirational information, and achievement information;
determine, based on the type of information to output, a channel for outputting the type of information as part of the behavioral coaching; and
output, via the channel, a notification including content of the type of information, wherein the instructions that cause the at least one processor to:
determine the channel for outputting the type of information comprise instructions that cause the at least one processor to select, based on one or more rules, a particular surface on which to output the notification including content of the type of information,
select the particular surface comprise instructions that cause the at least one processor to select a display of a second computing device, the second computing device being different than the first computing device, and
output the notification via the channel comprise instructions that cause the at least one processor to output a request for the second computing device to output the notification.

9. The first computing device of claim 8, further comprising:
one or more sensors configured to generate data,
wherein the instructions that cause the at least one processor to obtain the contextual and fitness related information of the user comprise instructions that cause the at least one processor to obtain the contextual and fitness related information of the user based on the data generated by the one or more sensors.

10. The first computing device of claim 9, wherein the one or more sensors include a heart rate sensor.

11. The first computing device of claim 8, wherein the instructions that cause the at least one processor to determine the current motivational state of the user comprise instructions that cause the at least one processor to determine a first motivational state of the user at a first time, the memory further comprising instructions that cause the at least one processor to:
obtain, after the first time, second contextual and fitness related information of the user; and
determine, by inputting the second contextual and fitness related information into the model, a second motivational state of the user.

12. The first computing device of claim 11, wherein the instructions that cause the at least one processor to determine the second motivational state of the user comprise instructions that cause the at least one processor to:
obtain transition rules between the first motivational state and the second motivational state,
wherein the instructions that cause the at least one processor to determine the second motivational state of the user comprise instructions that cause the at least one processor to determine, based on the transition rules and the second contextual and fitness related information, that the user has transitioned to the second motivational state.

13. The first computing device of claim 12, wherein the instructions that cause the at least one processor to determine the type of information to output comprise instructions that cause the at least one processor to:
  determine, responsive to determining that the user has transitioned to the second motivational state, an initial type of information to output.

14. A non-transitory computer-readable storage medium storing instructions that, when executed, cause one or more processors of a first computing device to
  obtain user consent to collect and make use of personal information for providing behavioral coaching;
  obtain contextual and fitness related information of a user;
  determine, by inputting the contextual and fitness related information into a model that defines a motivational state, a current motivational state of the user;
  determine, based at least in part on the current motivational state of the user, a type of information to output as part of the behavioral coaching, wherein the type of information is selected from a group comprising education information, inspirational information, and achievement information;
  determine, based on the type of information to output, a channel for outputting the type of information as part of the behavioral coaching; and
  output, via the channel, a notification including content of the type of information, wherein the instructions that cause the one or more processors to:
  determine the channel for outputting the type of information comprise instructions that cause the one or more processors to select, based on one or more rules, a particular surface on which to output the notification including content of the type of information,
  select the particular surface comprise instructions that cause the one or more processors to select a display of a second computing device, the second computing device being different than the first computing device, and
  output the notification via the channel comprise instructions that cause the one or more processors to output a request for the second computing device to output the notification.

* * * * *